(12) United States Patent
Zhang

(10) Patent No.: US 6,416,982 B1
(45) Date of Patent: Jul. 9, 2002

(54) BIOLOGICAL FERTILIZER BASED ON YEASTS

(75) Inventor: Lingyu Zhang, Bethesda, MD (US)

(73) Assignee: Ultra Biotech Ltd., Douglas (GB)

( * ) Notice: Subject to any disclaimer, the term of this patent is extended or adjusted under 35 U.S.C. 154(b) by 0 days.

(21) Appl. No.: 09/655,144

(22) Filed: Sep. 5, 2000

(51) Int. Cl.⁷ .............................................. C12N 13/00
(52) U.S. Cl. .............................. 435/173.8; 424/93.21; 424/93.51
(58) Field of Search ........................ 424/93.21, 93.51; 435/173.8

(56) References Cited

U.S. PATENT DOCUMENTS

| | | | |
|---|---|---|---|
| 3,711,392 A | 1/1973 | Betzger | |
| 3,968,254 A | 7/1976 | Rhodes et al. | |
| 4,041,182 A | 8/1977 | Erickson et al. | |
| 4,119,429 A | 10/1978 | Lovness et al. | |
| 4,155,737 A | 5/1979 | Dommergues et al. | |
| 4,952,229 A | 8/1990 | Muir | |
| 4,985,060 A | 1/1991 | Higa | |
| 5,071,462 A | 12/1991 | Kimmra | |
| 5,312,632 A | 5/1994 | Simsa et al. | |
| 5,578,486 A | 11/1996 | Zhang | |
| 5,952,020 A | 9/1999 | Lizak | |
| 5,981,219 A | 11/1999 | Flugge et al. | |
| 6,159,510 A | 12/2000 | Lizak | |

FOREIGN PATENT DOCUMENTS

| | | |
|---|---|---|
| CN | 1081662 | 2/1994 |
| CN | 1082016 | 2/1994 |
| CN | 1082017 | 2/1994 |
| CN | 1102635 | 5/1995 |
| CN | 1103060 | 5/1995 |
| CN | 1109595 | 10/1995 |
| CN | 1110317 | 10/1995 |
| EP | 553 377 | 8/1993 |
| ES | 475500 | 11/1978 |
| FR | 2 489 363 | 3/1982 |
| SU | 220 916 | 3/1967 |
| WO | WO 95/04814 | 2/1995 |

OTHER PUBLICATIONS

Yarrow, D. Genus 22. Sacccharomyces Meyen ex Reess. 1984. In the Yeasts a Taxonomic Study. Kreger van Rij, N.J.W. (ed.). Elsevier Science Publishers B.V.—Amsterdam, IIIrd Edition, pp. 379–386.*
U.S. application No. 09/796,818, Cheung, filed Mar. 1, 2001.
U.S. application No. 09/796,819, Cheung, filed Mar. 1, 2001.
U.S. application No. 09/796,820, Cheung, filed Mar. 1, 2001.
U.S. application No. 09/796,821, Cheung, filed Mar. 1, 2001.
U.S. application No. 09/796,822, Cheung, Mar. 1, 2001.

Bassett CA. 1993 Beneficial effects of electromagnetic fields. J Cell Biochem. 51(4):387–93.
Bugbee et al. 1998. Leaching of nitrogen and phosphorus form potting media containing biosolids compost as affected by organic and clay amendments. Bull. Environ. Contam. Toxicol. 60:716–23.
Gonzalez et al. 1980 Effects of an electric field of sinusolidal waves on the amino acid biosynthesis by *Azotobacter*. Z. Naturforsch. 35c:258–61.
Goodman et al. 1995. Effects of electromagnetic fields on molecules and cells. *International Review of Cytology*. Eds. Kwang et al. Academic Press vol. 158, p279–339.
Greweling et al. 1960. Chemical soil tests. Cornell Experiment Station Bulletin 960:22–25.
Grospietsch et al. 1995. Stimulating effects of modulated 150 MHz electromagnetic fields on the growth of *Escherichia coli* in a cavity resonator. Bioelectrochemistry and Bioenergetics. 37:17–23.
Grundler W. 1978. Nonthermal effects of millimeter microwaves on yeast growth. Z. Naturforsch. 33c:15–22.
Grundler et al. 1982. Resonant–like dependence of yeast growth rate on microwave frequencies. Br J Cancer Suppl. 45(5):206–8.
Grundler W. 1989. Resonant microwave effect on locally fixed yeast microcolonies. Z. Naturforsch. 44c:863–66.
Grundler et al. Mechanisms of electromagnetic interaction with cellular systems. Naturwissenschafter 79:551–559.
Hsui–Che et al. 1994. Experimental Results of TLB in Tropical Country–Malaysia. *Academic Theses on TLB Complex Microbial Fertilizer*. Zhang, LY. eds. China Science and Technology Press. pp. 104–126.
Lin H et al. 1994. Specific region of the c–myc promoter is responsive to electric and magnetic fields. J Cell Biochem. 54(3):281–8.
Lunt et al. 1950. The Morgan soil testing system. *Connecticut Agricultureal Experiment Station*, New Haven, Connecticut. Bulletin 541.
Moore RL. 1979. Biological effects of magnetic fields:studies with microorganisms. Can. J. Microbiol. 25:1145–51.
Murphy et al. 1962. A modified single solution method for the determination of phosphate in natural waters. Anal. Chem. Acta 27:31–36.

(List continued on next page.)

Primary Examiner—Christopher R. Tate
Assistant Examiner—Kailash C. Srivastava
(74) Attorney, Agent, or Firm—Pennie & Edmonds LLP

(57) ABSTRACT

The present invention provides biological fertilizer compositions that comprise yeast cells that have an enhanced ability to fix atmospheric nitrogen, decompose phosphorus minerals and compounds, decompose potassium minerals and compounds, decompose complex carbon compounds, over produce growth factors, and over produce ATP. The biological fertilizer composition of the invention can replace mineral fertilizers in supplying nitrogen, phosphorus, and potassium to crop plants. Methods of manufacturing the biological fertilizer compositions and methods of uses are also encompassed.

20 Claims, 11 Drawing Sheets

OTHER PUBLICATIONS

Figure 1:
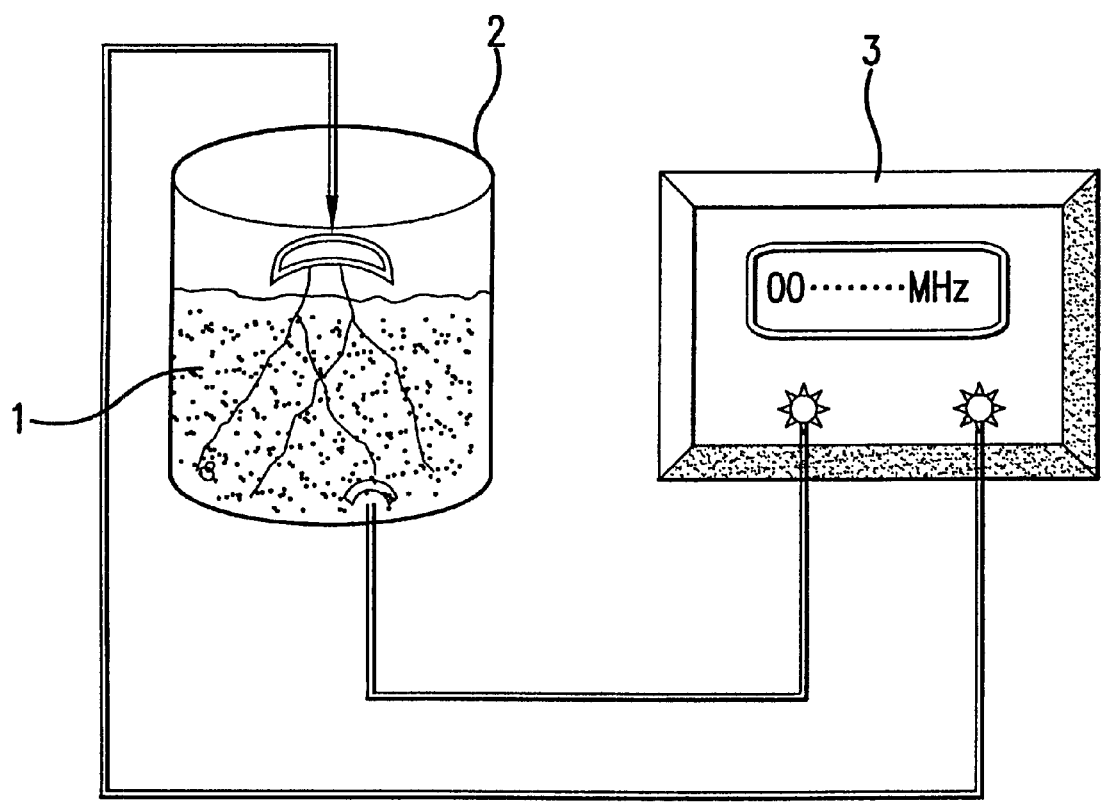

Norris et al. 1997. Do bacteria sing? Sonic intercellular communication between bacteria may reflect electromagnetic intracellular communication involving coherent collective vibrational modes that could integrate enzyme activities and gene expression. Mol Microbiol. 24(4):879–80.

Phillips JL. 1993. Effects of electromagnetic field exposure on gene transcription. J Cell Biochem. 51(4):381–6.

Puchyr et al. 1986. Determination of trace elements in foods by HCl–HNO3 leaching and flame atomic absorption spectroscopy. J. Assoc. Off. Anal. Chem. 69(5):868–70.

Romano–Spica et al. 2000. Ets1 oncogene induction by ELF–modulated 50 MHz radiofrequency electromagnetic field. Bioelectromagnetics. 21(1):8–18.

Zhang LY. 1994. Introduction to TLB, A Complex Microbial Fertilizer—Preliminary Application of MAB in Agriculture. *Academic Theses on TLB Complex Microbial Fertilizer*. Zhang, LY. eds. China Science and Technology Press. pp. 1–17.

Zhang et al. 1992. Electrostimulation of the dehydrogenase system of yeast by alternating currents. Bioelectrochemistry and Bioenergetics 28:341–53.

Verhasselt et al. 1995. New open reading frames, one of which is similar to the nifV gene of Azotobacter vinelandii, found on a 12.5 kbp fragment of chromosome IV of Saccharomyces cerevisiae. Yeast. (10):961–6.

* cited by examiner

BIOLOGICAL FERTILIZER BASED ON YEASTS

1. FIELD OF THE INVENTION

The invention relates to a biological fertilizer that comprises yeasts for fixing atmospheric nitrogen, and decomposing insoluble compounds containing phosphorus, potassium and/or carbon. The invention also relates to methods for manufacturing the biological fertilizer, and methods for using the biological fertilizer to increase crop yields.

2. BACKGROUND OF THE INVENTION

Use of fertilizer is essential in supporting the growth of high yield crops. Of the basic nutrients that plants need for healthy growth, large amounts of nitrogen (taken up as $NO_3^-$ or $NH_4^+$), phosphorus (taken up as $H_2PO_4^-$), and potassium (taken up as $K^+$) nutrients are required by most crops on most soils (Wichmann, W., et al., IFA World Fertilizer Use Manual). Such large amounts of nitrogen, phosphorus, and potassium nutrients are supplied mainly in the form of mineral fertilizers, either processed natural minerals or manufactured chemicals (K. F. Isherwood, 1998, Mineral Fertilizer Use and the Environment, United Nations Environmental Programme Technical Report No. 26.). The development and use of mineral fertilizers since the 1940s has permitted significant increases in crop yields on the same to slightly less amount of cropland to support today's enormous population. Without such advances in agriculture, a great amount of pastures and forests would have been converted into cropland. (K. F. Isherwood, 1998, Mineral Fertilizer Use and the Environment, United Nations Environmental Programme Technical Report No. 26.)

Despite the importance of mineral fertilizers in providing mankind with abundant agricultural products, the harm done to the environment has been recognized in the recent years. Mineral fertilizers may have incurred damages to soils. For example, most nitrogen fertilizers may acidify soils, thereby adversely affecting the growth of plants and other soil organisms. Extensive use of chemical nitrogen fertilizers may also inhibit the activity of natural nitrogen fixing microorganisms, thereby decreasing the natural fertility of soils. Mineral fertilizers may also introduce toxic substances into soil and produce. For example, phosphate fertilizers processed from rock phosphate often contain small amounts of toxic elements, such as cadmium, which may build up in soil and be taken up by plants. The long term use of mineral fertilizers may also cause severe environmental pollution. For example, the loss of nitrogen and phosphate fertilizers due to leaching and soil erosion has led to contamination of soil and ground water, and eutrophication of surface water. Cleaning up polluted soil and water has been a complicated and difficult task. The cost for such a task is also astronomical.

In search for a solution to the problem, some are going back to organic fertilizers. As is well known, organic fertilizers come from many different sources. Types of organic fertilizer include farm wastes, such as crop residues and animal manures; residues from plant and animal products, such as wood materials; and town wastes, such as sewage (Wichmann, W., et al., IFA World Fertilizer Use Manual). Organic fertilizers are usually low in nutrients and less effective in supporting plant growth. For example, the total nutrients in cattle manure is less than 2%, and the nitrogen nutrients therein are more difficult to be effectively utilized due to their losses into the environment (K. F. Isherwood, 1998, Mineral Fertilizer Use and the Environment, United Nations Environmental Programme Technical Report No. 26.). Normally, very large amount of organic fertilizers have to be applied to soil. To reach high crop yield, organic fertilizers have only been used to supplement mineral fertilizers. Therefore, the problems with mineral fertilizers cannot be satisfactorily solved by substituting mineral fertilizer with organic fertilizer. Furthermore, organic fertilizers also have created environmental problems. For example, some organic fertilizers, if unprocessed, contains pathogenic microorganisms, such as E. coli, Salmonella, and Coccidae. Organic fertilizers may also contain toxic chemicals and may produce undesirable odor. The use of organic fertilizer also contribute to the contamination and eutrophication of the natural water system. Therefore, in many parts of the world, including the United States, laws and regulations have been established imposing considerable restriction on both the composition and the usage of organic fertilizers.

Biological fertilizers utilizing microorganisms have been proposed as alternatives to mineral fertilizers. Naturally occurring nitrogen fixing microorganisms including bacteria, such as Rhizobium, Azotobacter, and Azospirillum, (See for example, U.S. Pat. No. 5,071,462) and fungi, such as *Aspergillus flavus-oryzae*, (See, for example, U.S. Pat. No. 4,670,037) have been utilized in biological fertilizers. Naturally occurring microorganisms capable of solubilizing rock phosphate ore or other insoluble phosphates into soluble phosphates have also been utilized in biological fertilizers either separately (e.g., U.S. Pat. No. 5,912,398) or in combination with nitrogen fixing microorganisms (e.g., U.S. Pat. No. 5,484,464). Genetically modified bacterial strains have also been developed and utilized in biological fertilizers. An approach based on recombinant DNA techniques has been developed to create more effective nitrogen fixing, phosphorus decomposing, and potassium decomposing bacterial strains for use in a biological fertilizer, see, for example, U.S. Pat. No. 5,578,486; PCT publication WO 95/09814; Chinese patent publication: CN 1081662A; CN 1082016A; CN 1082017A; CN 1103060A; and CN 1109595A.

However, the biological fertilizers that are based on naturally occurring microorganisms are generally not efficient enough to effectively replace mineral fertilizers. It is therefore important to develop biological fertilizers that can replace mineral fertilizers in supplying nitrogen, phosphorus, and potassium to crops for producing high quality agricultural products while avoiding the problems associated with mineral fertilizers. The present invention provides a biological fertilizer based on yeasts, which can replace mineral fertilizers.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

3. SUMMARY OF THE INVENTION

The present invention relates to biological fertilizers. The biological fertilizer compositions of the invention may comprise up to six different yeast cell components, an organic substrate component and/or an inorganic substrate component. In particular, the yeast cell components of the composition are capable of fixing atmospheric nitrogen, decomposing insoluble minerals or compounds, decomposing complex carbon materials or compounds, overproducing growth factors, or overproducing ATP, respectively.

The present invention uses yeasts that are commercially available and/or accessible to the public, such as but not limited to *Saccharomyces cerevisiae*. The yeast cell components of the invention are produced by culturing yeast cells under activation conditions such that the abilities of the cells to fix atmospheric nitrogen, to decompose insoluble phosphorus minerals or compounds, to decompose insoluble potassium minerals or compounds, and to decompose complex carbon materials or compounds are activated or enhanced. The yeast cells can also be cultured under conditions such that their abilities to produce excess growth factors or ATP are activated or enhanced. Yeast cells exhibiting such activities are useful in converting nitrogen from the atmosphere to nitrogenous compounds that can be used by plants as nutrients, releasing the otherwise insoluble phosphorus, potassium and carbon from minerals and complex molecules, such that these elements become available in a form that the plant can utilize for growth. Some yeast cells in the fertilizer are used for supporting other plant nutrient-providing yeast cells by supplying them with growth factors and ATP.

The present invention also involves the use of a wide variety of organic and inorganic materials in the fertilizer to support the growth of the yeast strains of the present invention. In one embodiment, the fertilizer is produced by mixing coal-mine waste and rock phosphate with the yeast strains. In another embodiment, the fertilizer is produced by mixing animal manures, and optionally, a biological disinfectant, with the yeast strains. In yet another embodiment, the fertilizer is produced by mixing sludge from sewage water treatment plant and a biological disinfectant with the yeast strains.

The invention also relates to methods for manufacturing the fertilizer comprising mixing, drying, and packing the yeast strains of the present invention and the organic and/or inorganic materials.

The invention further relates to methods for using the fertilizer of the present invention. The biological fertilizers of the present invention are used to support and enhance the growth and maturation of a wide variety of plants.

4. BRIEF DESCRIPTION OF FIGURES

FIG. 1. Activation of yeast cells. 1 yeast culture; 2 container; 3 electromagnetic field source.

Figure 2:
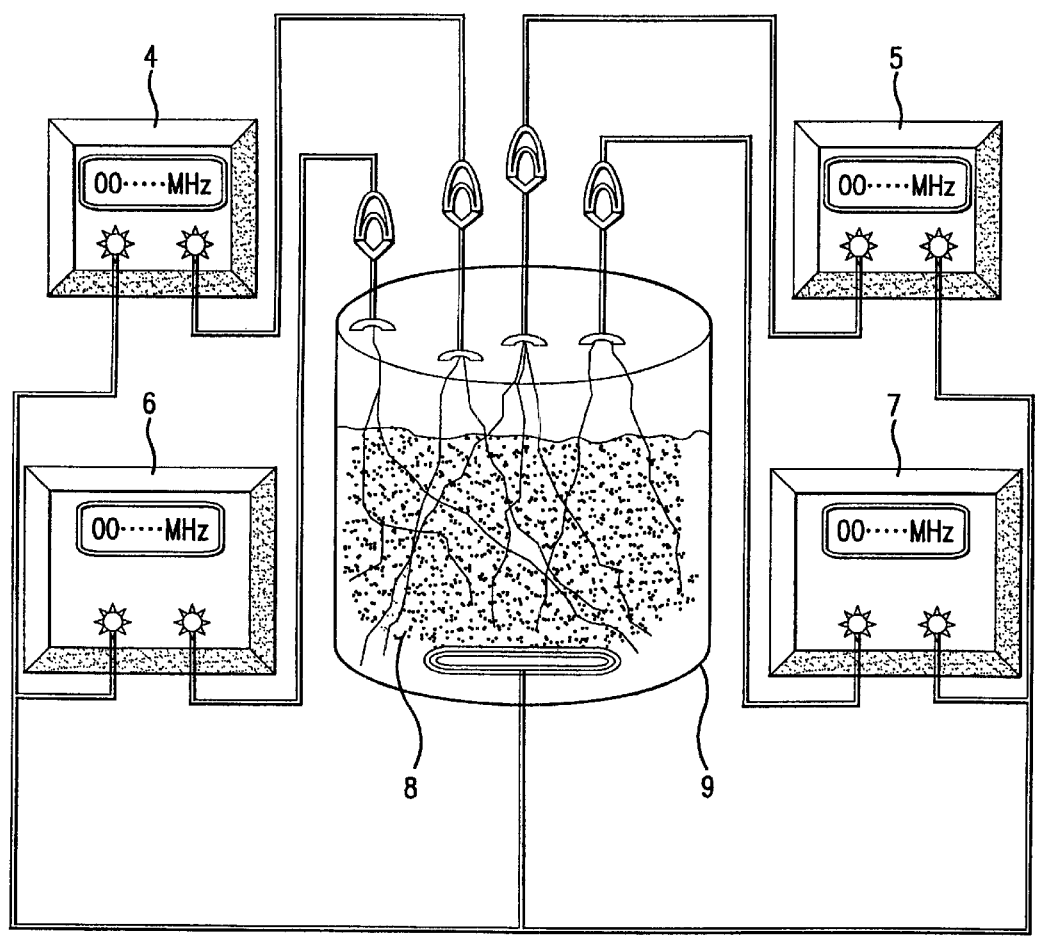

FIG. 2. Formation of symbiosis-like relationships among yeast strains. 4 electromagnetic field source for nitrogen-fixing yeast; 5 electromagnetic field source for P-decomposing yeast; 6 electromagnetic field source for K-decomposing yeast; 7 electromagnetic field source for C-decomposing yeast; 8 yeast culture; 9 container.

Figure 3:
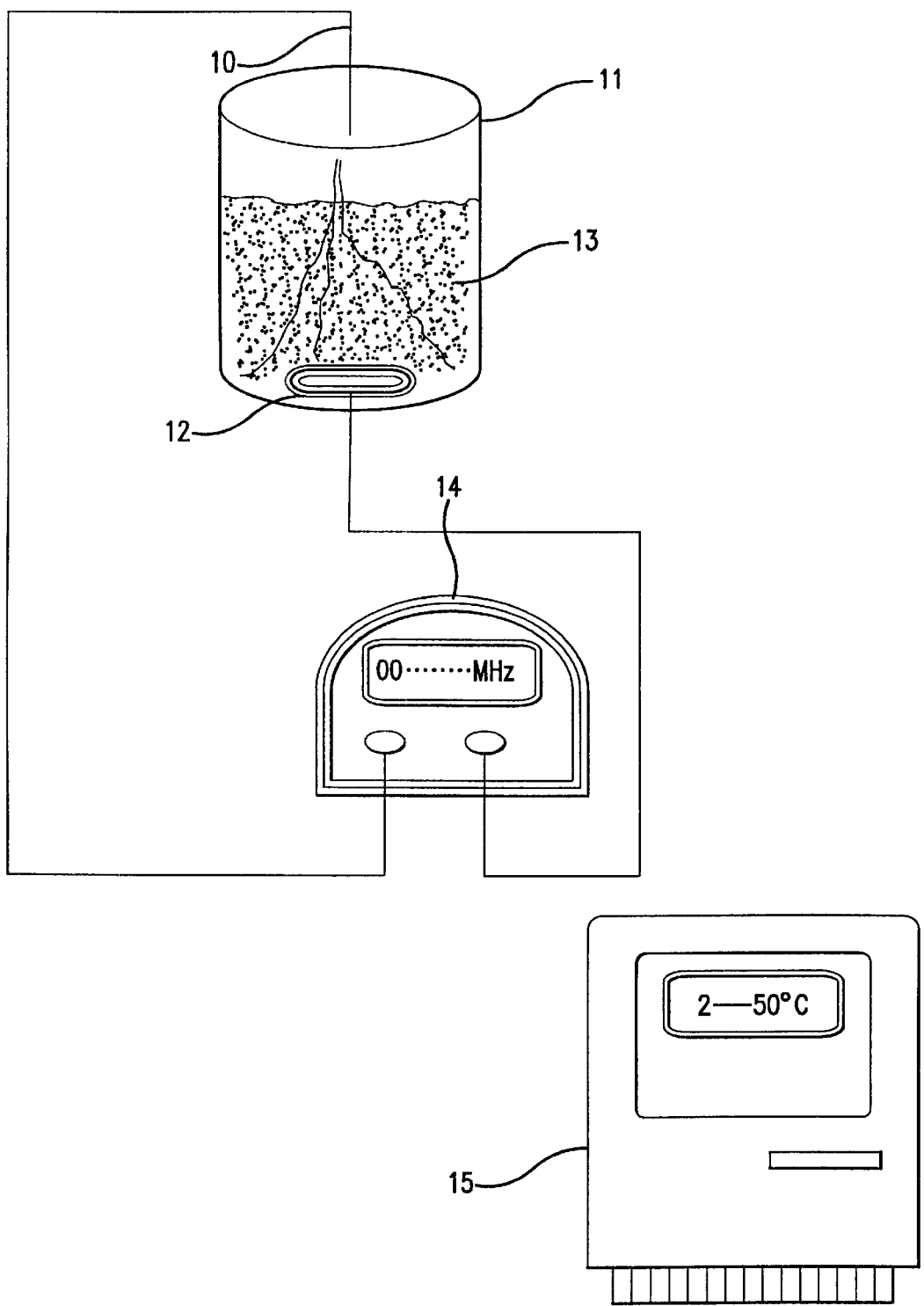

FIG. 3. Adaptation of yeast cells to a soil type. 10 electrode; 11 container; 12 electrode; 13 yeast culture; 14 electromagnetic field source; 15 temperature controller.

Figure 4:
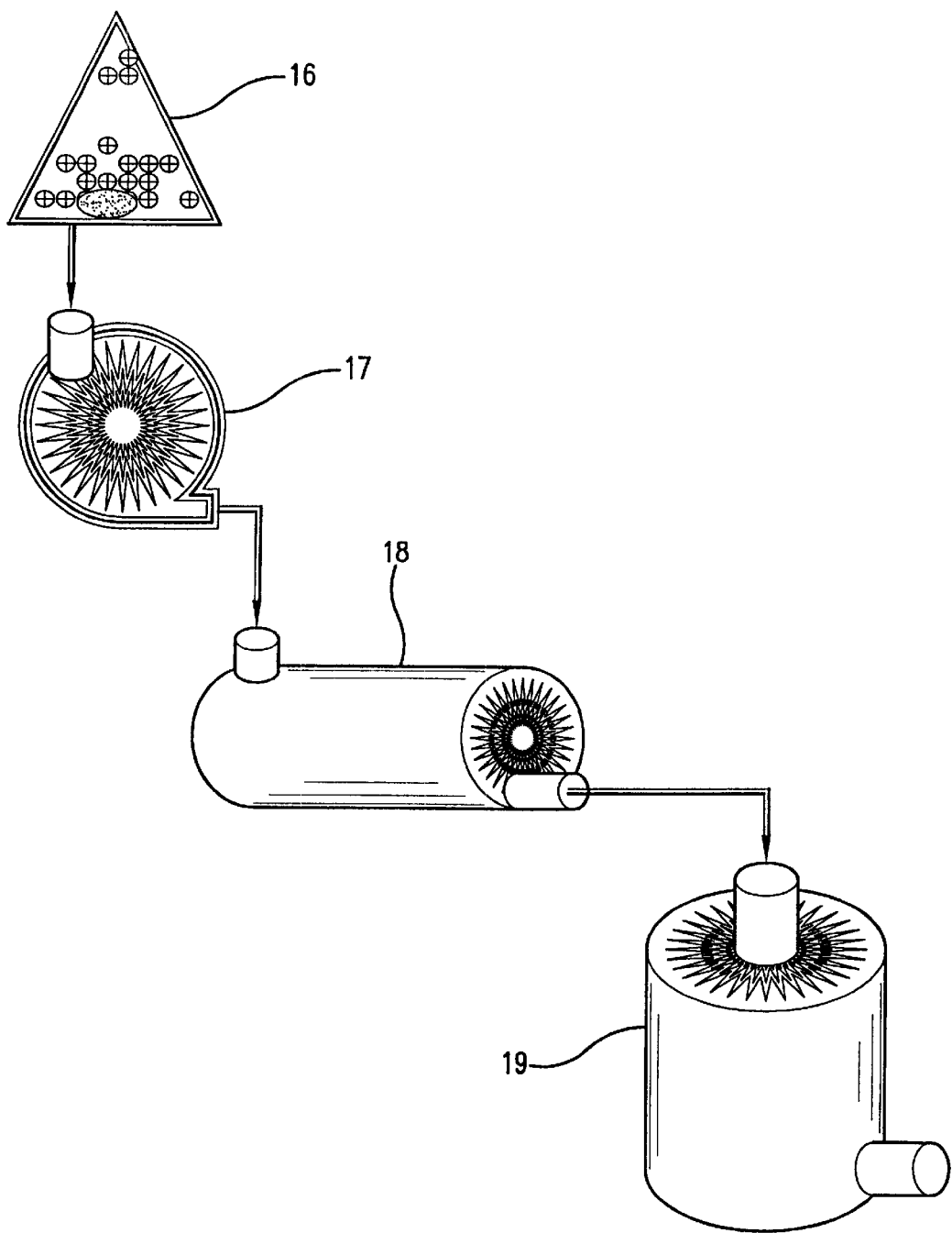

FIG. 4. Organic material grinding process. 16 organic raw material; 17 crusher; 18 grinder; 19 organic material in powder form.

Figure 5:
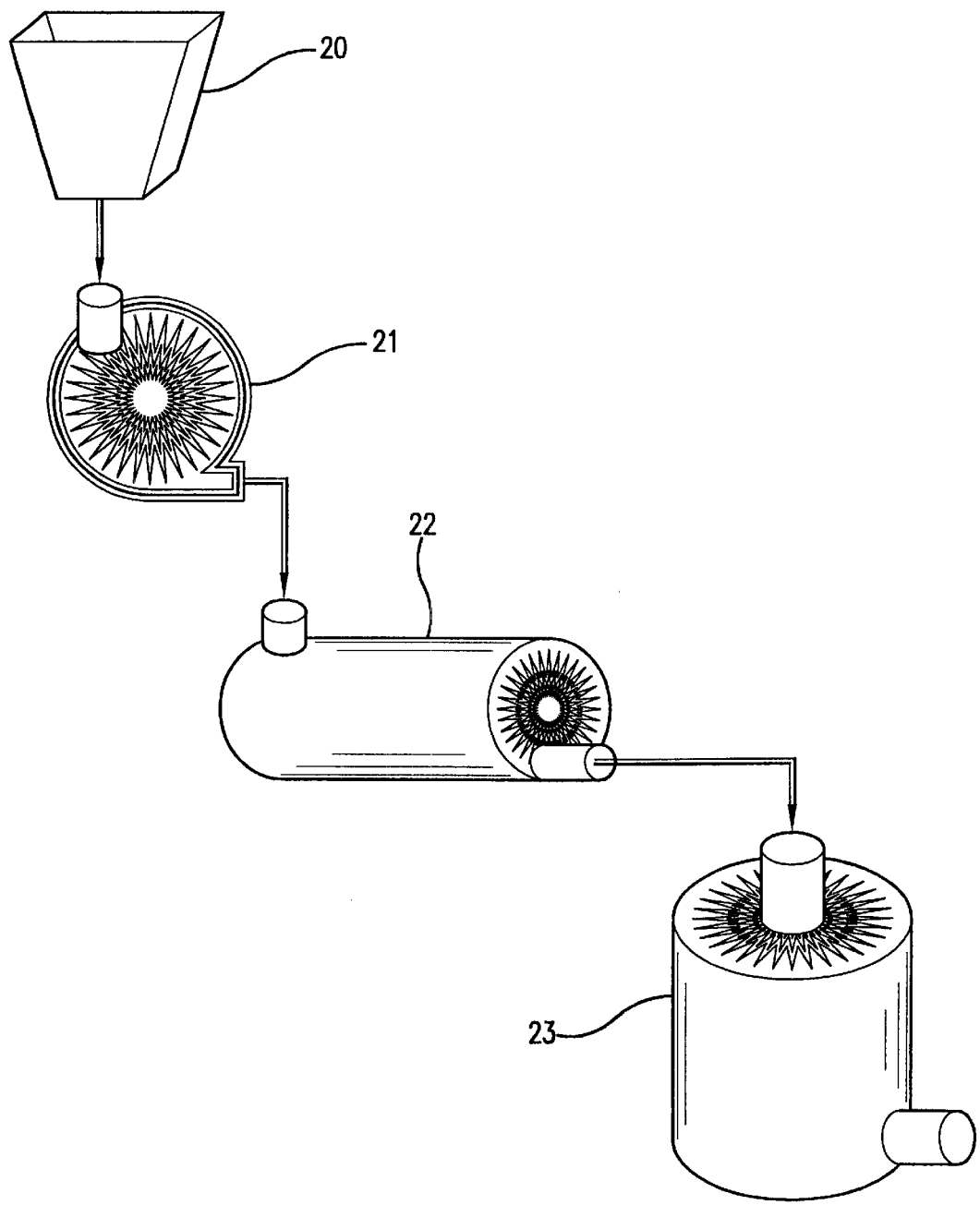

FIG. 5. Inorganic material grinding process. 20 inorganic raw material; 21 crusher; 22 grinder; 23 inorganic material in powder form.

Figure 6:
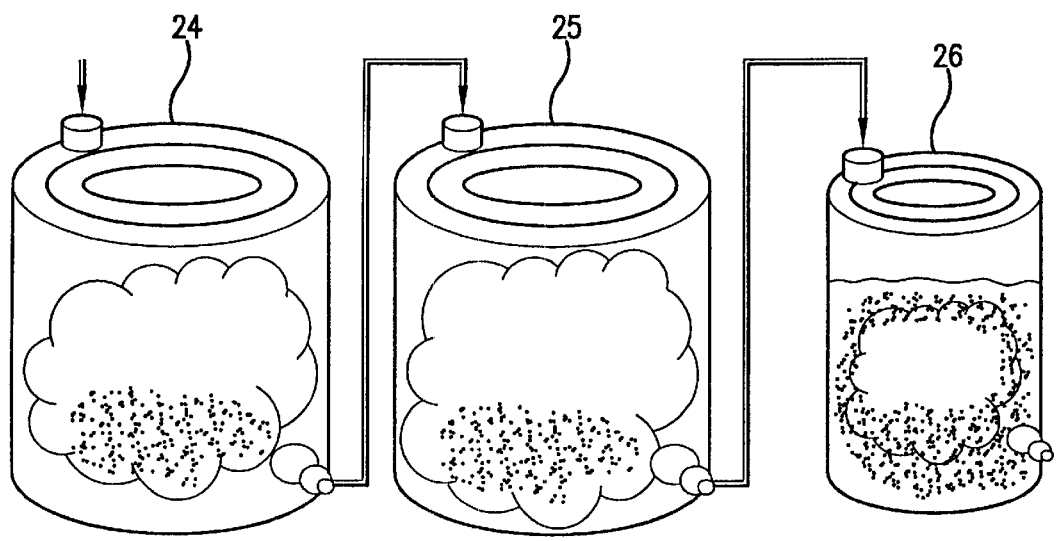

FIG. 6. Yeast fermentation process. 24 activated yeast cells; 25 tank for culturing yeast cells, starch: water (35° C.)=1:2.5, semi-aerobic fermentation at 28 to 30° C. for 48 to 72 hours; 26 harvested culture.

Figure 7:
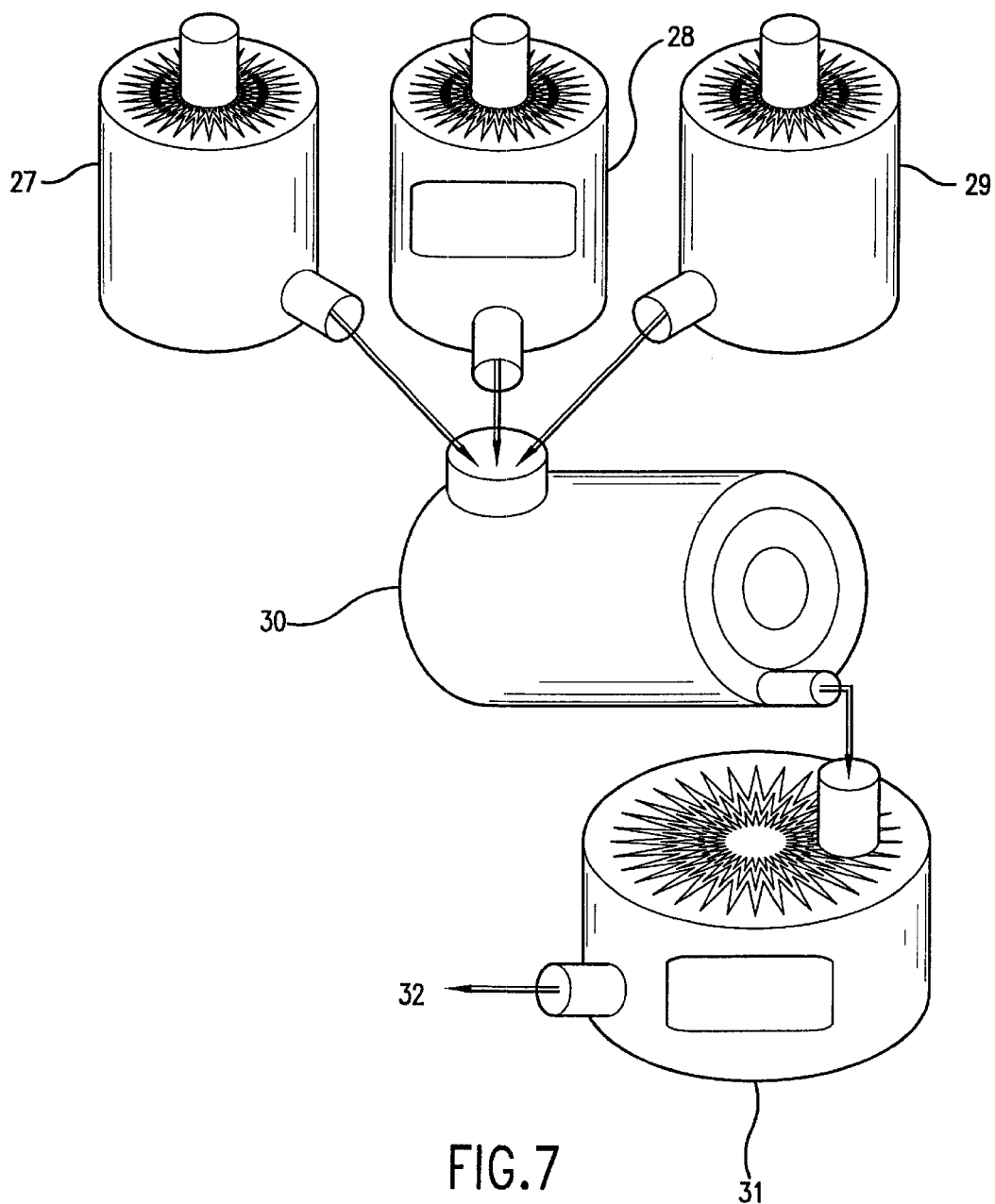

FIG. 7. Mixing organic and inorganic raw materials. 27 inorganic materials; 28 starch; 29 organic materials; 30 mixer; 31 mixture; 32 mixture to be transported to fertilizer production stage.

Figure 8:
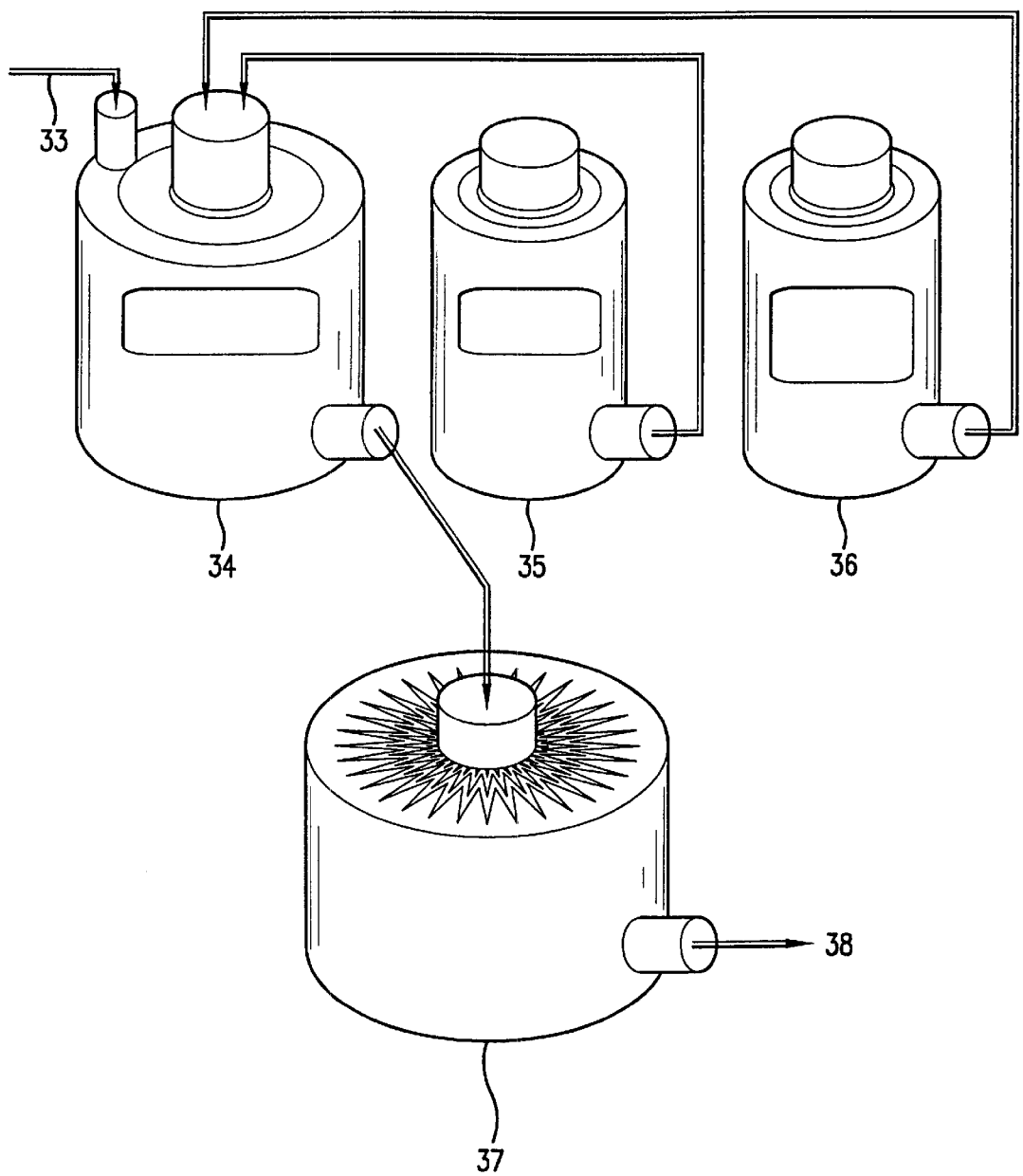

FIG. 8. Mixing yeast cells. 33 inlets for nitrogen-fixing, P-decomposing, K-decomposing, and C-decomposing yeasts; 34 mixing tank 35 ATP-producing yeast; 36 GP-producing yeast; 37 mixture of yeasts; 38 mixture to be transported to fertilizer production stage.

Figure 9:
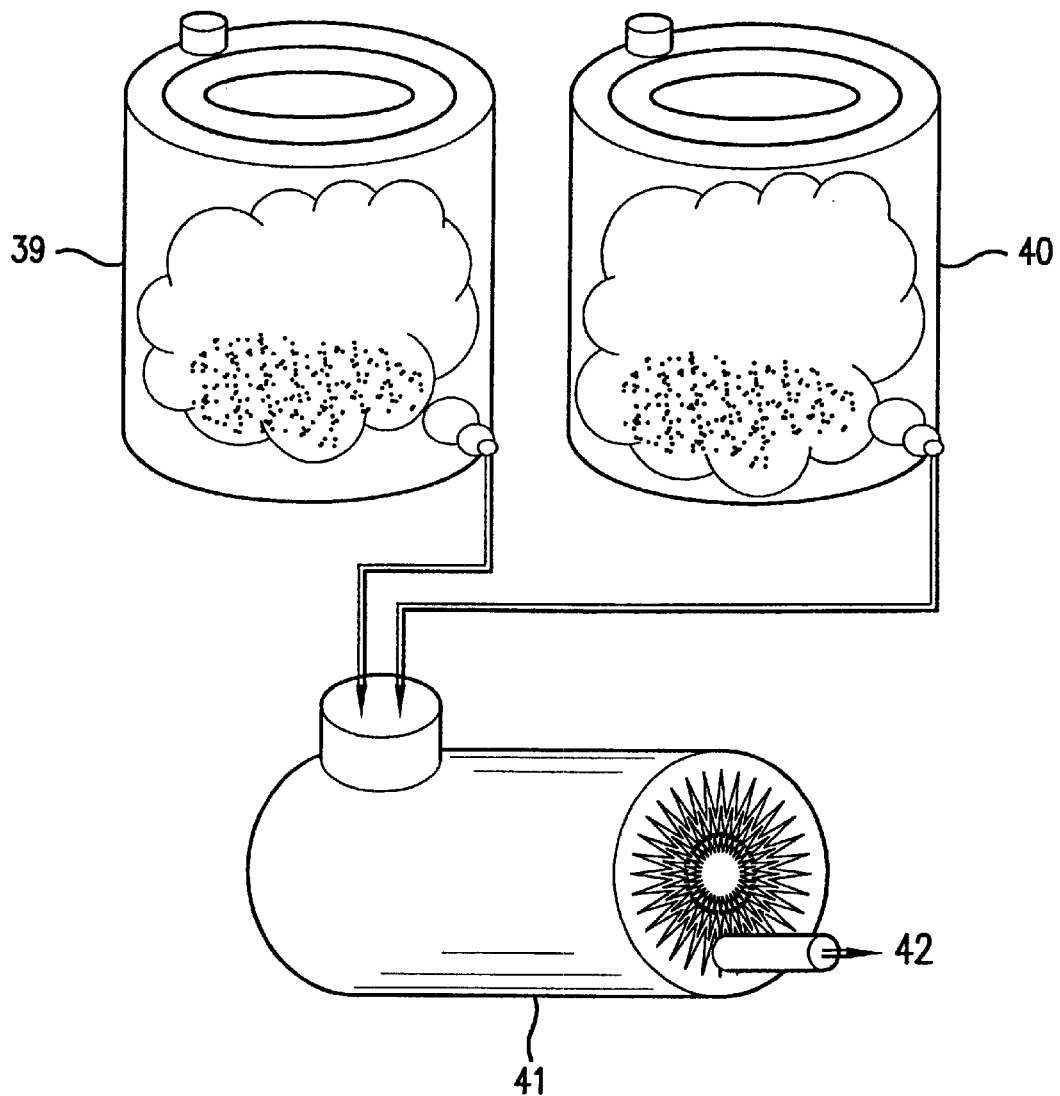

FIG. 9. Fertilizer production process. 39 mixture of yeast; 40 mixture of organic and inorganic materials; 41 granulizer; 42 fertilizer granules.

Figure 10:
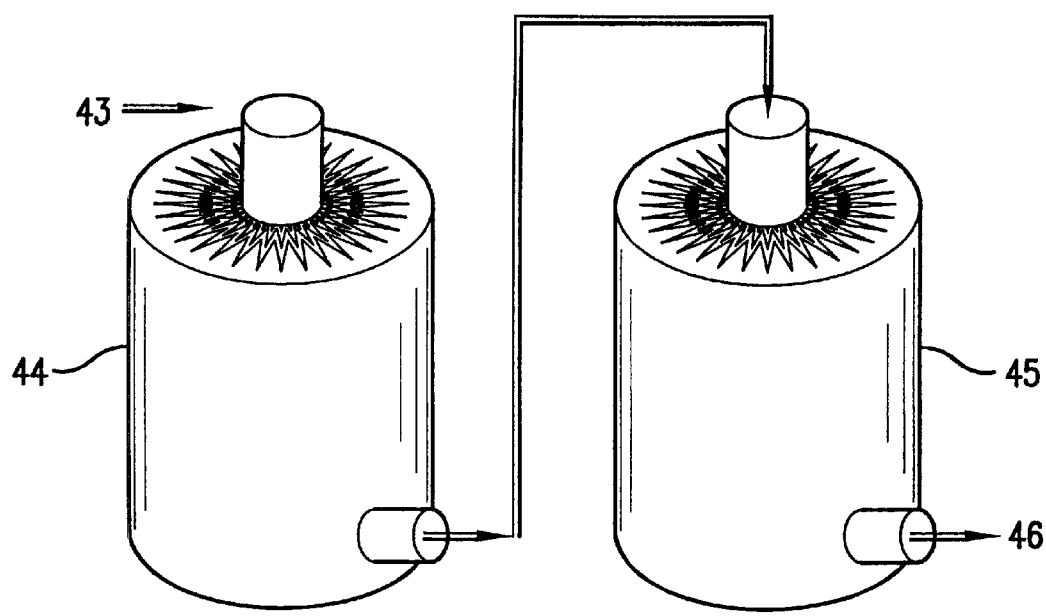

FIG. 10. Drying process. 43 fertilizer granules; 44 first dryer; 45 second dryer; 46 dried fertilizer.

Figure 11:
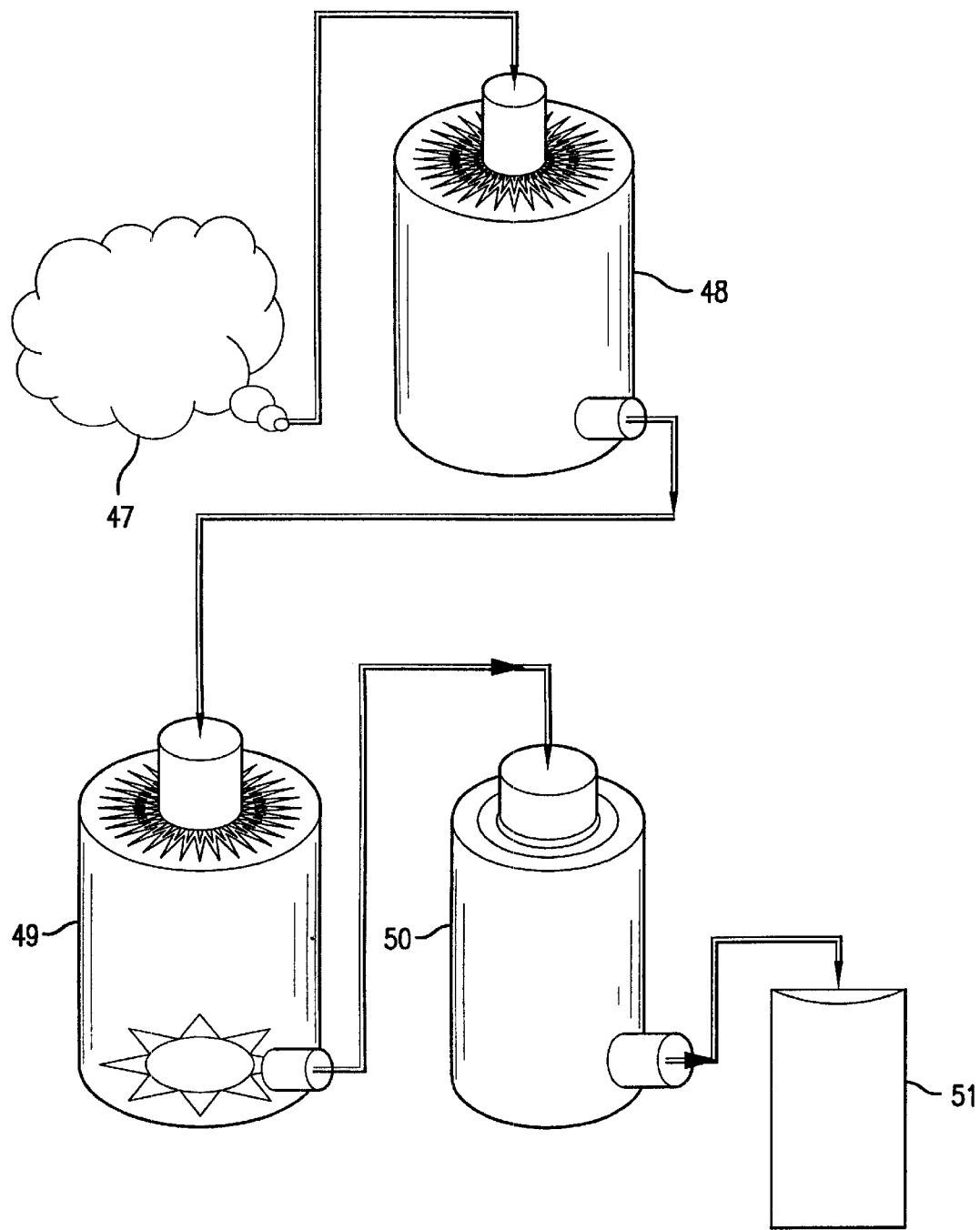

FIG. 11. Cooling and packaging process. 47 dried fertilizer; 48 cooler; 49 separator; 50 bulk bag filler; 51 final product.

5. DETAILED DESCRIPTION OF THE INVENTION

In one embodiment, the present invention provides biological fertilizer compositions that comprise yeast cells. The present invention also provides in various embodiments, methods for manufacturing the biological fertilizer compositions as well as methods for using the biological fertilizer compositions.

The biological fertilizer compositions of the invention can replace chemical/mineral fertilizers in supplying nitrogen (N), phosphorus (P), and potassium (K) to plants, especially crop plants. The biological fertilizer compositions of the present invention can increase crop yields by 10–60%. Because the biological fertilizers of the present invention utilize metabolic activities of living yeasts to convert raw materials, such as atmospheric nitrogen and phosphorus and potassium minerals, into plant nutrients, the conversion and release of such nutrients by the yeast cells is regulated in part by the nutrient content of the soil. The nutrient content of the soil in turn depends in part on both the environment and the changing needs of plants. Therefore, the release of plant nutrients by the biological fertilizer compositions is adaptable to the soil condition and can be sustained over a period of time.

In one embodiment, the biological fertilizer compositions of the invention comprise one or more yeast cell components. A yeast cell component of the biological fertilizer compositions comprises a plurality of yeast cells which are capable of performing one of the following functions, each of which results in the provision of one type of nutrients to plants: (1) fixation of atmospheric nitrogen; (2) decomposition of phosphorus minerals or compounds; (3) decomposition of potassium minerals or compounds; (4) decomposition of complex or high molecular weight carbon materials or compounds. Additional yeast cell components can be included to produce growth factors and ATP to support the other yeasts in the fertilizer compositions.

The biological fertilizer compositions of the invention can further comprises an organic substrate component, and/or an inorganic substrate component. The organic substrate component of the fertilizer compositions is a primary carbon source for the yeast cells in the fertilizer. The inorganic substrate component provides the yeast cells in the fertilizer compositions minerals, materials, and compounds containing phosphorus and/or potassium. The organic and inorganic substrate component may also provide the plants with other minerals such as but not limited to calcium, magnesium, and sulfur; and micronutrients, such as but not limited to boron, copper, iron, manganese, molybdenum, and zinc.

As used herein, the term "nitrogen fixation" or "fixation of atmospheric nitrogen" encompasses biological processes in which molecular nitrogen or nitrogen in the atmosphere is converted into one or more nitrogenous (N) compounds, including but not limited to, ammonia, ammonium salts, urea, and nitrates.

As used herein, the phrase "decomposition of phosphorus minerals or compounds" refers to biological processes which convert phosphorus (P) compounds, such as but not limited to those water-insoluble phosphorus compounds present in rock phosphate, into one or more different phosphorus compound(s) which can be more readily used for survival and/or growth by plants and other yeasts. For example, the resulting phosphorus compounds may be more soluble in water, and can thus be taken up by the roots of plants.

As used herein, the phrase "decomposition of potassium minerals or compounds" refers biological processes which convert potassium (K) compounds, such as but not limited to those water-insoluble potassium compounds present in potassium mica, into one or more different potassium compound(s) which can be more readily used for survival and/or growth by plants and other yeasts. For example, the resulting potassium compounds may be more soluble in water, and can thus be taken up by the roots of plants.

As used herein, the phrase "decomposition of complex or high molecular weight carbon minerals, materials or compounds" refers to the biological conversion of a complex organic or inorganic carbon molecule into one or more carbon molecule(s) which usually are of a lower molecular weight, and can be more readily used for survival and/or growth by plants and other organisms, including other yeasts. For example, it encompasses the conversion of high molecular weight carbon compounds in weathered coal to simple carbohydrates, such as pentose and hexose. This process includes those reactions where long chains of carbon atoms in a polymeric carbon compound are cleaved.

As used herein, the term "growth factors" refers to molecules commonly required for growth of yeasts, including but not limited to vitamins, in particular, vitamin B complexes, e.g., vitamin B-1, riboflavin (vitamin B-2), vitamin B-12, niacin (B-3), pyridoxine (B-6), pantothenic acid (B-5); folic acid; biotin; para-aminobenzoic acid; choline; and inositol.

A wide variety of organic and inorganic materials may be used to supply the phosphorus, potassium, and complex high molecular weight carbon minerals, materials and compounds to be converted by the yeast cells into nutrients for use by the yeasts and the plants. The organic and inorganic materials that may be used in conjunction with the present invention include, but are not limited to, minerals, such as but not limited to phosphate rock or rock phosphate, apatite, phosphorite, sylvinite, halite, camalitite, potassium mica, lignite; industrial materials or wastes, such as but not limited to coal-mine waste, weathered coal, coal-powder, and hydrocarbon waste; environmental materials and wastes, such as but not limited to sludge from sewage water treatment plant and land fills, muds, such as turf mud, mud from river and lake bed; organic wastes, such as but not limited to waste and manure from urban areas and animal manure, such as poultry manure, cattle manure, hog manure, sheep manure, and guano, waste materials from plants, waste material from animals including fish meal, bone meal, human waste, dried blood, etc., and products or by-products from fermentation of plant materials containing cellulose, starch and/or other carbohydrates.

In addition, depending on needs, a disinfectant may be included in the biological fertilizer compositions. An environmentally safe disinfectant is preferred. For example, a biological disinfectant, super-$CM_{61}$ can be used with environmental and organic wastes, such as waste and manure from urban areas and animal manure.

In various embodiments, the biological fertilizer compositions of the present invention comprises at least one yeast cell component, and preferably six yeast cell components. The inventor discovered that, under certain culture conditions, various yeast strains can be induced to exhibit the following six activities: (1) fixation of atmospheric nitrogen; (2) decomposition of phosphorus minerals or compounds; (3) decomposition of potassium minerals or compounds; (4) decomposition of complex or high molecular weight carbon materials or compounds; (5) production of excess growth factors in an amount that is sufficient to support the needs of other yeast strains in the fertilizer composition; and (6) production of excess ATP in an amount that is sufficient to support the needs of other yeast strains in the fertilizer composition. The culture condition determines the activity which is activated or enhanced in the cultured yeasts. The specific culture conditions for each of the six activities are described in details in sections 5.1–5.6 respectively.

According to the invention, a yeast cell component of the biological fertilizer is produced by culturing a plurality of yeast cells in an appropriate culture medium in the presence of an electromagnetic field. The electromagnetic field can be generated by various means well known in the art. A schematic illustration of an exemplary setup is depicted in FIG. 1. The electromagnetic field of a desired frequency and amplitude is generated by an electromagnetic source (3) which comprises one or more signal generators that are capable of generating electromagnetic waves, preferably sinusoidal waves, in the frequency range of 100 MHz–2000 MHz. If desirable, a signal amplifier can also be used to increase the output. The electromagnetic field can be applied to the culture by a variety of means including placing the culture in close proximity to the signal emitters. In one embodiment, the electromagnetic field is applied by electrodes that are submerged in the culture (1). In a preferred embodiment, one of the electrodes is a metal plate, and the other electrode comprises a plurality of wires configured inside the container (2) so that the energy of the electromagnetic field can be evenly distributed in the culture. The number of electrode wires used depends on both the volume of the culture and the diameter of the wire. In preferred embodiments, for a culture having a volume up to 5000 ml, one electrode wire having a diameter of between 0.1–1.2 mm can be used for each 100 ml of culture; for a culture having a volume greater than 1000 l, one electrode wire having a diameter of between 3–30 mm can be used for each 1000 l of culture.

The types of yeasts contemplated for use in the invention include without limitation, yeasts of the genera of Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis; Geotrichum, Hansenula, Kloeckera, Lipomyces, Pichia, Rhodosporidium, and Rhodotorula. Non-limiting examples of yeast strains include *Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.14, AS2.16, AS2.56, AS2.69, AS2.70, AS2.93, AS2.98 AS2.101, AS2.109, AS2.110, AS2.112, AS2.139, AS2.173, AS2.174, AS2.182, AS2.196 AS2.242, AS2.336, AS2.346, AS2.369, AS2.374, AS2.375, AS2.379, AS2.380, AS2.382, AS2.390, AS2.393, AS2.395, AS2.396, AS2.397, AS2.398, AS2.399, AS2.400, AS2.406, AS2.408, AS2.409, AS2.413, AS2.414, AS2.415, AS2.416, AS2.422, AS2.423, AS2.430, AS2.431, AS2.432, AS2.451, AS2.452, AS2.453, AS2.458, AS2.460, AS2.463, AS2.467, AS2.486, AS2.501, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI 1001, IFFI 1002, IFFI 1005, IFFI 1006, IFFI 1008, IFFI 1009, IFFI 1010, IFFI 1012, IFFI 1021, IFFI 1027, IFFI 1037, IFFI 1042, IFFI 1043, IFFI 10451, IFFI 1048, IFFI 1049, IFFI 1050, IFFI 1052, IFFI 1059, IFFI 1060, IFFI 1063, IFFI 1202, IFFI 1203, IFFI 1206, IFFI 1209, IFFI 1210, IFFI 1211, IFFI 1212, IFFI 1213, IFFI 1215, IFFI 1220, IFFI 1221, IFFI 1224, IFFI 1247, IFFI 1251, IFFI 1270, IFFI 1277, IFFI 1287, IFFI 1289, IFFI 1290, IFFI 1291, IFFI 1291, IFFI 1292, IFFI 1293, IFFI 1297, IFFI 1300, IFFI 1301, IFFI 1302, IFFI 1307, IFFI 1308, IFFI 1309, IFFI 1310, IFFI 1311, IFFI 1331, IFFI 1335, IFFI 1336, IFFI 1337, IFFI 1338, IFFI 1339, IFFI 1340, IFFI 1345, IFFI 1348, IFFI 1396, IFFI 1397, IFFI 1399, IFFI 1411, IFFI 1413, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces chevalieri* Guillermond, AS2.131, AS2.213; *Saccharomyces delbrueckii* Lindner, AS2.2 85; *Saccharomyces delhrueckii* Lindner ver. mongolicus Lodder, AS2.209, AS2.1157; *Saccharomyces exiguus* Hansen, AS2.349, AS2.1158; *Saccharomyces fermentati* (Saito) Lodder et van Rij, AS2.286, AS2.343; *Saccharomyces logos* van laer et Denamur ex Jorgensen, AS2.156, AS2.327, AS2.335; *Saccharomyces mellis* Lodder et Kreger Van Rij, AS2.195; *Saccharomyces microellipsoides* Osterwalder, AS2.699; *Saccharomyces oviformis* Osterwalder, AS2.100; *Saccharomyces rosei* Lodder et kreger van Rij, AS2.287; *Saccharomyces rouxii* Boutroux, AS2.178, AS2.180, AS2.370, AS2.371; *Saccharomyces sake* Yabe, ACCC2045; *Saccharomyces uvarum* Beijer, IFFI 1023, IFFI 1032, IFFI 1036, IFFI 1044, IFFI 1072, IFFI 1205, IFFI 1207; *Saccharomyees willianus* Saccardo, AS2.5, AS2.7, AS2.119, AS2.152, AS2.293, AS2.381, AS2.392, AS2.434, AS2.614, AS2.1189; Saccharomyces sp., AS2.311; *Saccharomyces ludwigii* Hansen, ACCC2044, AS2.243, AS2.508; *Saccharomyces sinenses* Yue, AS2.1395; *Schizosaccharomyces octosporus* Beijerinck, ACCC 2046, AS2.1148; *Schizosaccharomyces pombe* Linder, ACCC2047, ACCC2048, AS2.248, AS2.249, AS2.255, AS2.257, AS2.259, AS2.260, AS2.274, AS2.994, AS2.1043, AS2.1149, AS2.1178, IFFI.1056; *Sporobolomyces roseus* Klyver et van Niel, ACCC 2049, ACCC 2050, AS2.619, AS2.962, AS2.1036; *Sporobolomyces salmonicolor* (Fischer et Brebeck) Kluyver et van Niel, ACCC2051, AS2.261, AS2.262; *Torulopsis candida*(Saito)Lodder, ACCC2052, AS2.270; *Torulopsis famta* (Harrison)Lodder et van Rij, ACCC2053, AS2.685; *Torulopsis globosa* (Olson et Hammer)Lodder et van Rij, ACCC2054, AS2.202; *Torulopsis inconspicua* Lodder et van Rij, AS2.75; *Trichosporon behrendoo* Lodder et Kreger van Rij, ACCC2055, AS2.1193; *Trichosporon capitatum* Diddens et Lodder, ACCC2056, AS2.1385; *Trichosporon cutaneum*(de Beurm et al.)Ota, ACCC2057, AS2.25, AS2.570, AS2.571, AS2.1374; *Wickerhamia fluoresens* (Soneda) Soneda, ACCC2058, AS2.1388; *Ashbya gossypii* (Ashby et Nowell) Guillermond, ACCC2001, AS2.475, AS2.1176; *Blastomyces dermatitidis* Gilehrist et Stikes, ID(D 10)23; *Candida albicans* (Robin) Berkhout, ACCC2002, AS2.538, ID 16u (C1)u, ID 61v(C1)v; *Candida arborea*, AS2.566; *Candida guillermondii*(Castellani) Langeron et guerra, AS2.63, ID 21 a(C5)a, ID 21 b(C5)b; *Candida Krusei* (Castellani) Berkhout, AS2.1045; *Candida lambica*(Lindner et Genoud) van.Uden et Buckley, AS2.1182; *Candida lipolytica* (Harrison) Diddens et Lodder, AS2.1207, AS2.1216, AS2.1220, AS2.1379, AS2.1398, AS2.1399, AS2.1400; *Candida parakrusei* (Castellani et Chalmer) Langeron et Guerra, ID 19 a(C4)a, ID 19 b(C4)b, ID 19 c(C4)c, ID 19 d(C4)d; *Candida parapsilosis* (Ashford) Langeron et Talice, AS2.590; *Candida parapsilosis* (Ashford) et Talice Var.imtermedia Van Rij et Verona, AS2.491; *Candida pseudotropicalis* (Castellani) Basgal, AS2.68, ID64(C3); *Candida pulcherrima* (Lindner) Windisch, AS2.492; *Candida robusta* Diddens et Lodder, AS2.1195; *Candida rugousa* (Anderson) Diddens et Loddeer, AS2.511, AS2.1367, AS2.1369, AS2.1372, AS2.1373, AS2.1377, AS2.1378, AS2.1384; *Candida tropicalis* (Castellani) Berkout, ACCC2004, ACCC2005, ACCC2006, AS2.164, AS2.402, AS2.564, AS2.565, AS2.567, AS2.568, AS2.617, AS2.637, AS2.1387, AS2.1397, ID 17 a($C_2$)a, ID 17 b($C_2$)b, ID 17 d($C_2$)d; *Candida utilis* Henneberg Lodder et Kreger Van Rij, AS2.120, AS2.281, AS2.1180; *Citeromyces matritensis* (Santa Maria) Santa Maria, AS2.1401; *Crebrothecium ashbyii* (Guillermond) Routein, ACCC2013, ACCC2014, AS2.481, AS2.482, AS2.1197; *Cryptococcus laurentii* (Kufferath) Skinner, ACCC2007, AS2.114, ID 95 ($y_2$); *Cryptococcus neoformans* (Sanfelice) Vuillemin, ID 25 u($D_2$)u, ID 25 v($D_2$)v, ID 25 w($D_2$)w; *Debaryomyces hansenii* (Zopf) Lodder et Kreger-van Rij, ACCC2010, AS2.45; *Debaryomyces kloeckeri* Guilliermond et Peju, ACCC2008, ACCC2009, AS2.33, AS2.34, AS2.494; Debaryomyces sp., ACCC2011, ACCC2012; *Endomycopsis fibuligera* (Lindner) Dekker, ACCC2015, AS2.1145; *Eremothecium ashbyii* Guilliermond; *Geotrichum candidum* Link, ACCC2016, AS2.361, AS2.498, AS2.616, AS2.1035, AS2.1062, AS2.1080, AS2.1132, AS2.1175, AS2.1183; *Geotrichum ludwigii* (Hansen) Fanfet al., AS2.363; *Geotrichum robustum* Fang et al., ACCC2017, AS2.621; *Geotrichum suaveolens* (Krzemecki) Fang et al., AS2.364; *Hansenula anomala* (Hansen) H et P sydow, ACCC2018, AS2.294, AS2.295, AS2.296, AS2.297, AS2.298, AS2.299, AS2.300, AS2.302, AS2.338, AS2.339, AS2.340, AS2.341, AS2.470, AS2.592, AS2.641, AS2.642, AS2.735, AS2.782, AS2.794; *Hansenula arabitolgens* Fang, AS2.887; *Hansenula jadinii* Wickerham, ACCC2019; *Hansenula saturnus* (Klocker) H et P sydow, ACCC2020, AS2.303; *Hansenula schneggii* (Weber) Dekker, AS2.304; *Hansenula subpelliculosa* Bedford, AS2.740, AS2.760, AS2.761, AS2.770, AS2.783, AS2.790, AS2.798, AS2.866; *Kloeckera apiculata* (Reess emend. Klocker) Janke, ACCC2021, ACCC2022, ACCC2023, AS2.197, AS2.496, AS2.711, AS2.714; *Lipomyces starkeyi* Lodder et van Rij, ACCC2024, AS2.1390, *Pichia farinosa* (Lindner) Hansen, ACCC2025, ACCC2026, AS2.86, AS2.87, AS2.705, AS2.803; *Pichia membranaefaciens* Hansen, ACCC2027, AS2.89, AS2.661, AS2.1039; *Rhodosporidium toruloides* Banno, ACCC2028, AS2.1389; *Rhodotorula aurantiaca* (Saito) Lodder, ACCC2029, AS2.280; *Rhodotorula glutinis* (Fresenius) Harrison, ACCC2030, AS2.102, AS2.107, AS2.278, AS2.499, AS2.694, AS2.703, AS2.704, AS2.1146; *Rhodotorula minuta* (Saito) Harrison, AS2.277; *Rhodotorula rubar* (Demme) Lodder, ACCC2031, AS2.21, AS2.22, AS2.103, AS2.105, AS2.108, AS2.140, AS2.166, AS2.272, AS2.279, AS2.282; *Rhodotorula sinesis* Lee, AS2.1391; *Saccharomyces bailii* Lindner, AS2.312; and *Saccharomy-* ces carlsbergensis Hansen, ACCC2032, ACCC2033, AS2.113, AS2.116, AS2.118, AS2.121, AS2.132, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042.

Certain yeast species that can be activated according to the present invention and are included in the present invention are known to be pathogenic to human and/or other living organisms, for example, *Ashbya gossypii* (Ashby et Nowell) Guillermond, ACCC2001, AS2.475, AS2.1176; *Blastomyces dermatitidis* Gilehrist et Stikes, ID(D 10)23; *Candida albicans* (Robin) Berkhout, ACCC2002, AS2.538, ID 16u(C1)u, ID 61v(C1)v; *Candida parakrusei* (Castellani et Chalmer) Langeron et Guerra, ID 19 a(C4)a, ID 19 b(C4)b, ID 19 c(C4)c, ID 19 d(C4)d; *Candida tropicalis* (Castellani) Berkout, ID 17 a($C_2$)a, ID 17 b($C_2$)b, ID 17 d($C_2$)d; *Citeromyces matritensis* (Santa Maria) Santa Maria, AS2.1401; *Crebrothecium ashbyii* (Guillermond) Routein, ACCC2013, ACCC2014; *Cryptococcus laurentii* (Kufferath) Skinner, ACCC2007, AS2.114, ID 95 ($y_2$); *Cryptococcua neoformans* (Sanfelice) Vuillemin, ID 25 u($D_2$)u, ID 25 v($D_2$)v, ID 25 w($D_2$)w; *Debaryomyces hansenii* (Zopf) Lodder et Kreger-van Rij, ACCC2010; *Debaryomyces Kloeckeri* Guilliermond et Peju, ACCC2008, ACCC2009; *Debaryomyces sp.*, ACCC2011, ACCC2012; *Endomycopsis fibuligera* (Lindner) Dekker, ACCC2015, AS2.1145. Under certain circumstances, it may be less preferable to use such pathogenic yeasts in the biological fertilizer of the invention, for example, if such use in an open field may endanger the health of human and/or other living organisms.

Yeasts of the Saccharomyces genus are generally preferred. Among strains of *Saccharomyces cerevisiae*, *Saccharomyces cerevisiae* Hansen is a preferred strain. The most preferred strains of yeast are *Saccharomyces cerevisiae* Hansen strains having accession numbers AS2.501, AS2.535, AS2.441, AS2.406, AS2.382, and AS2.16 as deposited at the China General Microbiological Culture Collection Center (CGMCC). Generally, the yeast strains can be obtained from private or public laboratory cultures, or publically accessible culture deposits, such as the American Type Culture Collection, 10801 University Boulevard, Manassas, V. 20110-2209 and the China General Microbiological Culture Collection Center (CGMCC), China Committee for Culture Collection of Microorganisms, Institute of Microbiology, Chinese Academy of Sciences, Haidian, P.O. Box 2714, Beijing, 100080, China.

Although it is preferred, the preparation of the yeast cell components of the invention is not limited to starting with a pure strain of yeast. Each yeast cell component may be produced by culturing a mixture of yeast cells of different species or strains. The constituents of a yeast cell component can be determined by standard yeast identification techniques well known in the art.

Some yeasts may perform one of the desired functions more efficiently than others. The ability of any species or strain of yeast to perform one of the six desired functions before or after culturing under the conditions of the invention can readily be tested by methods known in the art. For example, the amount of nitrogen fixed can be determined by a modified acetylene reduction method as described in U.S. Pat. No. 5,578,486 which is incorporated herein by reference in its entirety. The modified acetylene reduction method determines the amount of nitrogen fixed by measuring the decrease in molecular nitrogen in a volume of air. The amount of nitrogen fixed can also be determined by measurement of the ammonia and nitrates produced by the yeast cells (see, for example, Grewling et al., 1965, Cornell Agr Exp Sta Bull 960:22–25). For the other functions, the amount of phosphorus available to plants as a result of conversion from insoluble or biologically-unavailable phosphorus compounds can be determined by the molybdenum blue method (see, for example, Murphy et al., 1962, Analytica Chimica Acta 27:31–36) or the UV absorption method; whereas the amount of available potassium converted from insoluble or biologically-unavailable potassium compounds can be determined, for example, by flame atomic absorption spectroscopy (see, for example, Puchyr, et al., 1986, J. Assoc. Off. Anal. Chem. 69:868–870). The ability of the yeasts to supply plant available N, P, and K after the biological fertilizer composition has been added to soil can be tested by many techniques known in the art. For example, plant-available ammonia, nitrates, P, and K produced by the yeast cells in soil can be extracted and quantitatively analyzed by the Morgan soil test system (see, for example, Lunt et al., 1950, Conn Agr Exp Sta Bull 541).

Without being bound by any theory or mechanism, the inventor believes that the culture conditions activate and/or enhance the expression of a gene or a set of genes in yeast such that the yeast cells become active or more efficient in performing the respective functions.

According to the invention, the biological fertilizer compositions comprises at least one yeast cell component capable of performing one of the following biological functions: (1) fixation of atmospheric nitrogen; (2) decomposition of insoluble or biologically-unavailable phosphorus minerals or compounds present in the fertilizer composition or in soil; (3) decomposition of insoluble or biologically-unavailable potassium minerals or compounds present in the fertilizer composition or in soil; (4) decomposition of complex or high molecular weight carbon materials or compounds present in the fertilizer composition or in soil; (5) production of excess growth factors in an amount that is sufficient to support the needs of other yeast strains in the fertilizer composition; and (6) production of excess ATP in an amount that is sufficient to support the needs of other yeast strains in the fertilizer composition. In preferred embodiments, the biological fertilizer compositions can comprise from one yeast strain to up to six different yeast species or strains, each cultured under specific conditions to induce or maximize its ability to perform the respective functions. It will be understood that alternative formulations are also contemplated. Thus, if desired, the biological fertilizer composition may omit one or more of the above-described yeast cell components. For example, in soil rich in biologically-available phosphorus, a fertilizer composition may be formulated to lack the component consisting of phosphorus compounds-decomposing yeast. In the most preferred embodiments of the present invention, a biological fertilizer composition that contains all six yeast cell components as well as the organic and/or inorganic substrates is contemplated.

In another embodiment of the invention, where the yeast cells of the various yeast cell components are present in a mixture, the yeast cells can be cultured under certain conditions such that the yeast cells with different functions can supply each other with and/or rely on each other for nutrients and growth factors. As a result, a symbiosis-like relationship is established among the various yeast cell components in the fertilizer compositions of the invention. This culturing process is optional but can improve the stability and efficiency of the biological fertilizer such that the fertilizer is made more suitable for long term use in natural soil environments. The culturing conditions for this optional process are described in Section 5.7.

In yet another embodiment of the invention, the yeast cells may also be cultured under certain conditions so as to adapt the yeast cells to a particular type of soil. This culturing process is optional, and can be applied to each yeast cell component separately or to a mixture of yeast cell components. The result is better growth and survival of the yeasts in a particular soil environment. The culturing conditions for this optional process are described in Section 5.8.

As used herein, the biological fertilizer composition supports or enhances plant growth, if in the presence of the biological fertilizer in the soil, or applied to the roots, stems, leaves or other parts of the plant, the plant or a part of the plant gains viability, size, weight, rate of germination, rate of growth, or rate of maturation. Thus, the biological fertilizer compositions have utility in any kind of agricultural, horticultural, and forestry practices. The biological fertilizer compositions can be used for large scale commercial farming, in open fields or in greenhouse, or even in interiors for decorative plants. Preferably, the biological fertilizer is used to enhance the growth of crop plants, such as but not limited to cereal crops, vegetable crops, fruit crops, flower crops, and grass crops. For example, the biological fertilizer may be used with wheat, barley, corn, soybean, rice, oat, potato, apple, orange, tomato, melon, cherry, lemon, lettuce, carrot, sugar cane, tobacco, cotton, etc.

The biological fertilizer compositions may be applied in the same manner as conventional fertilizers. As known to those skilled in the relevant art, many methods and appliances may be used. In one embodiment, culture broths of the yeast strains of the present invention are applied directly to soil or plants. In another embodiment, dried powders of the yeast strains of the present invention are applied to soil or plants. In yet another embodiment, mixtures of the yeast cell components and organic and inorganic substrate components of the present invention are applied to soil or plants. The biological fertilizer compositions may be applied to soil, by spreaders, sprayers, and other mechanized means which may be automated. The biological fertilizer compositions may be applied directly to plants, for example, by soaking seeds and/or roots, or spraying onto leaves. Such application may be made periodically, such as once per year, or per growing season, or more frequently as desired. The biological fertilizer compositions of the invention can also be used in conjunction or in rotation with other types of fertilizers.

Described respectively in Sections 5.1–5.6 are the yeast cell components used for nitrogen fixation, phosphorus compound decomposition, potassium compound decomposition, complex carbon compound decomposition, growth factors production, and ATP production. Methods for preparing each yeast cell components are described. Section 5.7 describes the methods for establishing a symbiosis-like relationship among yeast strains in a fertilizer composition of the invention. Section 5.8 describes methods for adapting yeast cells of the invention to a particular type of soil. Section 5.9 describes the manufacture of the biological fertilizer compositions. Methods for the preparation of organic and inorganic raw materials and for the manufacture of the biological fertilizer, including mixing, drying, cooling, and packing, are also described. In various embodiments of the invention, standard techniques for handling, transferring, and storing microorganisms are used. Although it is not necessary, sterile conditions or clean environments are desirable when carrying out the processes of the invention.

5.1. NITROGEN-FIXING YEAST CELL COMPONENT

Nitrogen fixation is a process whereby atmospheric nitrogen is converted into ammonia and nitrates. Close to 800 species of naturally occurring microorganisms, mostly bacteria and cyanobacteria, from more than 70 genera have been found to be able to fix nitrogen. Some of the nitrogen-fixing microorganisms, such as Rhizoboum, form symbiotic association with plants, especially in the root of legumes. Others, such as Azotobacter, are free-living and capable of fixing nitrogen in soil.

In the present invention, the ability of yeast to fix nitrogen is activated or enhanced, and the resulting nitrogen-fixing yeast cells can be used as a component of the biological fertilizer composition of the invention.

According to the invention, yeast cells that have an enhanced ability to fix nitrogen are prepared by culturing the cells in the presence of an electromagnetic field in an appropriate culture medium. The frequency of the electromagnetic field for activating or enhancing nitrogen fixation in yeasts can generally be found within the range of 800 MHz–1000 MHz. After the yeast cells have been cultured for a sufficient period of time, the cells can be tested for their ability to fix nitrogen by methods well known in the art.

The method of the invention for making the nitrogen-fixing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1%. These carbon sources can be used individually, or several such carbon sources may be combined in the medium.

Among the inorganic salts which can be incorporated in the culture media are the customary salts capable of yielding sodium, potassium, calcium, phosphate, sulfate, carbonate, and like ions. Non-limiting examples of nutrient inorganic salts are $CaCO_3$, $KH_2PO_4$, $MgSO_4$, $NaCl$, and $CaSO_4$.

TABLE I

Composition for a culture medium for nitrogen-fixing yeast

| Medium Composition | Quantity |
|---|---|
| $KH_2PO_4$ | 0.2 g |
| $K_2HPO_4$ | 0.2 g |
| $MgSO_4 \cdot 7H_2O$ | 0.25 g |
| $CaCO_3 \cdot 5H_2O$ | 3.5 g |
| $CaSO_4 \cdot 2H_2O$ | 0.5 g |
| NaCl | 0.25 g |
| Yeast extract paste | 0.3 g |
| Sucrose | 12.0 g |
| Distilled water or autoclaved water | 1000 ml |

It should be noted that the composition of the media provided in Table I is not intended to be limiting. Various modifications of the culture medium may be made by those skilled in the art, in view of practical and economic considerations, such as the scale of culture and local supply of media components.

The process is initiated by inoculating each 100 ml of medium with 1 ml of an inoculum of the selected yeast strain(s) at a cell density of $10^2$–$10^5$ cell/ml, preferably $3 \times 10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 860 to 870 MHz, preferably at about 865 MHz, more preferably in the range of 865.522 to 865.622 MHz, and most preferably at 865.572 MHz. The amplitude of the field is in the range of 1000–2000 mV, preferably at about 1250 mV. After this first period of culture, the yeast cells are further incubated under substantially the same conditions for approximately another 24 hours, except that the amplitude is increased to a higher level in the range of 4000–5000 mV, preferably to about 4656 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the nitrogen-fixing yeast cells may be recovered from the culture by various methods known in the art, and stored at a temperature below about 0° C. to 4° C. The nitrogen-fixing yeast cells may also be dried and stored in powder form.

Any methods known in the art can be used to test the cultured yeast cells for their ability to fix nitrogen. For example, a modified acetylene reduction method for measuring nitrogen fixed by microorganisms is used to evaluate the nitrogen-fixing capability of the prepared yeast. The modified acetylene reduction method is described in U.S. Pat. No. 5,578,486 which is incorporated herein by reference in its entirety. For example, 1 ml of the prepared yeast culture is inoculated into 30 ml of a medium according to Table I in a sealed 250 ml flask. The culture is incubated at a temperature in the range of 20–28° C. for 24–56 hours in the presence of air containing about 20% by volume oxygen and 80% by volume nitrogen. The amount of nitrogen fixed can then be determined by measuring the decrease in nitrogen from the air by any means known in the art, such as but not limited to gas chromatography. The amount of nitrogen fixed by the yeast cells of the invention is at least about 10 mg for each gram of yeast dry weight. For example, after activation, the amount of nitrogen fixed by *Saccharomyces cerevisiae* Hansen strain AS2.501, can reach about 11200 mg/g.

5.2. PHOSPHORUS-DECOMPOSING YEAST CELL COMPONENT

The phosphorus compound-decomposing (P-decomposing) yeast of the invention converts insoluble or biologically-unavailable phosphorus-containing substances, such as rock phosphate, into soluble phosphorous compounds so that they become available to plants.

In the present invention, the ability of yeast to decompose insoluble phosphorus-containing substances is activated or enhanced, and the resulting P-decomposing yeast cells can be used as a component of the biological fertilizer composition of the invention.

According to the invention, yeast cells that are capable of P-decomposing are prepared by culturing the cells in the presence of an electromagnetic field in an appropriate culture medium. The frequency of the electromagnetic field for activating or enhancing P-decomposition in yeasts can generally be found in the range of 300 MHz to 500 MHz. After the cells have been cultured for a sufficient period of time, the cells can be tested for their ability to decompose phosphorus-containing substances by methods well known in the art.

The method of the invention for making the P-decomposing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1.5%. These carbon sources can be used individually, or several such carbon sources may be combined in the medium.

Among the inorganic salts which can be incorporated in the culture media are the customary salts capable of yielding sodium, potassium, calcium, sulfate, carbonate, and like ions. Non-limiting examples of nutrient inorganic salts are $CaCO_3$, $MgSO_4$, $NaCl$, and $CaSO_4$. Insoluble phosphorus-containing substances in a suitable form are also included in the media. Non-limiting examples include powder of rock phosphate of $\geq 200$ mesh. Other insoluble phosphorus-containing substances can also be used either separately or in combination.

TABLE II

Composition for a culture medium for P-decomposing yeast

| Medium Composition | Quantity |
|---|---|
| Sucrose | 15 g |
| NaCl | 1.2 g |
| $MgSO_4 \cdot 7H_2O$ | 0.2 g |
| $CaCO_3 \cdot 5H_2O$ | 3.0 g |
| $CaSO_4 \cdot 2H_2O$ | 0.3 g |
| $KNO_3$ | 0.3 g |
| Yeast extract paste | 0.5 g |
| Rock phosphate | 1.2 g; Powder of >200 mesh |
| Autoclaved water | 1000 ml |

It should be noted that the composition of the media provided in Table II is not intended to be limiting. Various modifications of the culture medium may be made by those skilled in the art, in view of practical and economic considerations, such as the scale of culture and local supply of media components.

The process is initiated by inoculating each 100 ml of medium with 1 ml of an inoculum of the selected yeast strain(s) at a cell density of $10^2$–$10^5$ cell/ml, preferably $3\times10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 360 to 370 MHz, preferably at about 366 MHz, more preferably in the range of 366.199 to 366.287 MHz, and most preferably at 366.243 MHz. The amplitude of the field is in the range of 1000 to 200 mV, preferably at about 1230 mV. After this first period of culture, the yeast cells are further incubated under substantially the same conditions for approximately another 24 hours, except that the amplitude is increased to a higher level in the range of 4000 to 5000 mV, preferably to about 4570 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the P-decomposing yeast cells may be recovered from the culture by various methods known in the art, and stored at a temperature below about 0° C. to 4° C. The P-decomposing yeast cells may also be dried and stored in powder form.

Any methods known in the art can be used to test the cultured yeast cells for their ability to decompose insoluble phosphorus-containing substances. In one embodiment, 1 ml of the prepared yeast culture is inoculated into 30 ml of a medium according to Table II. The culture is incubated at a temperature in the range of 20–28° C. for 24–56 hours. The amount of biologically available phosphorus in the form of $PO_4^{3-}$ in the culture can then be determined by any methods known in the art, including but not limited to UV absorption spectroscopy. The amount of $PO_4^{3-}$ in the culture is increased by at least 10 mg for each gram of yeast dry weight. For example, after activation, the amount of $PO_4^{3-}$ in a culture of *Saccharomyces cerevisiae* Hansen strain AS2.535 is increased to about 4460 mg/g.

5.3. POTASSIUM-DECOMPOSING YEAST CELL COMPONENT

The potassium cornpound-decomposing (K-decomposing) yeast of the invention converts insoluble potassium-containing substances, such as potassium mica, into soluble potassium so that they become available to plants.

In the present invention, the ability of a plurality of yeast cells to decompose insoluble potassium-containing substances is activated or enhanced, and the resulting K-decomposing yeast cells can be used as a component of the biological fertilizer composition of the invention.

According to the present invention, yeast cells that are capable of K-decomposing are prepared by culturing the cells in the presence of an electromagnetic field in an appropriate culture medium. The frequency of the electromagnetic field for activating or enhancing K-decomposition in yeasts can generally be found in the range of 100 MHz–300 MHz. After the yeast cells have been cultured for a sufficient period of time, the cells can be tested for their ability to decompose potassium-containing substances by methods well known in the art.

The method of the invention for making the K-decomposing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1.5%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $CaCO_3$, $MgSO_4$, NaCl, and $CaSO_4$. Insoluble potassium-containing substances in a suitable form are also included in the media. Non-limiting examples include powder of potassium mica of ≧200 mesh. Other insoluble potassium-containing substances can also be used either separately or combined.

TABLE III

Composition for a culture medium for K-decomposing yeast

| Medium Composition | Quantity |
| --- | --- |
| Sucrose | 15 g |
| NaCl | 1.2 g |
| MgSO$_4$•7H$_2$O | 0.2 g |
| CaCO$_3$•5H$_2$O | 3.0 g |
| CaSO$_4$•2H$_2$O | 0.3 g |
| (NH$_4$)$_2$HPO$_4$ | 0.3 g |
| Yeast extract paste | 0.3 g |
| Potassium mica | 1.2 g, Powder of >200 mesh |
| Autoclaved water | 1000 ml |

It should be noted that the composition of the media provided in Table III is not intended to be limiting. Various modifications of the culture medium may be made by those skilled in the art, in view of practical and economic considerations, such as the scale of culture and local supply of media components.

The process is initiated by inoculating each 100 ml of medium with 1ml of an inoculum of the selected yeast strain(s) at a cell density of $10^2$–$10^5$ cell/ml, preferably $3 \times 10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 250–260 MHz, preferably at about 255 MHz, more preferably in the range of 255.388 to 255.462 MHz, and most preferably at 255.425 MHz. The amplitude of the field is in the range of 1000–2000 mV, preferably at about 1340 mV. After this first period of culture, the yeast cells are further incubated under substantially the same conditions for approximately another 24 hours, except that the amplitude is increased to a higher level in the range of 4000–5000 mV, preferably to about 4850 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the K-decomposing yeast cells may be recovered from the culture by various methods known in the art, and stored at a temperature below about 0–4° C. The K-decomposing yeast cells may also be dried and stored in powder form.

Any methods known in the art can be used to test the cultured yeast cells for their ability to decompose insoluble potassium-containing substances. In one embodiment, 1 ml of the prepared yeast culture is inoculated into 30 ml of a medium according to Table III. The culture is incubated at a temperature in the range of 20–28° C. for 24–56 hours. The amount of biologically available potassium in the form of K$^+$ in the culture can then be determined by any methods known in the art, including but not limited to atomic absorption spectrometry. The amount of $K^+$ in the culture is increased by at least 10 mg for each gram of yeast dry weight. For example, after activation, the amount of $K^+$ in a culture of *Saccharomyees cerevisiae* Hansen strain AS2.441 can reach about 4050 mg/g.

5.4. COMPLEX CARBON-DECONPOSING YEAST CELL COMPONENT

The carbon-decomposing (C-decomposing) yeast of the invention converts complex, usually high molecular weight, carbon compounds and materials, such as cellulose, into simple carbohydrates, such as pentoses and hexoses. Such simple carbohydrates are utilized by other yeast cells to support their growth and activities.

In the present invention, the ability of yeast to decompose complex carbon compounds very efficiently is activated or enhanced, and the resulting C-decomposing yeast cells can be used as a component of the biological fertilizer composition of the invention.

According to the present invention, yeast cells that are capable of C-decomposition are prepared by culturing the cells in the presence of an electromagnetic field in an appropriate culture medium. The frequency of the electromagnetic field for C-decomposition in yeasts can generally be found in the range of 1000 MHz–1200 MHz. After the yeast cells have been cultured for a sufficient period of time, the cells can be tested for their ability to decompose complex carbon compounds by methods well known in the art.

The method of the invention for making the C-decomposing yeast cells is carried out in a liquid medium. The medium contains sources of nutrients assimilable by the yeast cells. Complex carbon-containing substances such as cellulose, coal, etc., in a suitable form can be used as sources of carbon in the culture medium. The exact quantity of the carbon source or sources utilized in the medium depends in part upon the other ingredients of the medium but, in general, the amount of carbohydrate usually varies between about 0.1% and 5% by weight of the medium and preferably between about 0.1% and 1%, and most preferably about 0.5%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $CaCO_3$, $MgSO_4$, $NaCl$, and $CaSO_4$.

TABLE IV

Composition for a culture medium for C-decomposing yeast

| Medium Composition | Quantity |
|---|---|
| Cellulose | 5.0 g; Powder of >100 mesh |
| NaCl | 0.6 g |
| $MgSO_4 \cdot 7H_2O$ | 0.3 g |
| $CaCO_3 \cdot 5H_2O$ | 1.5 g |
| $CaSO_4 \cdot 2H_2O$ | 0.4 g |
| $(NH_4)_2HPO_4$ | 0.3 g |
| Yeast extract paste | 0.5 g |
| $K_2HPO_4$ | 0.5 g |
| Autoclaved water | 1000 ml |

It should be noted that the composition of the media provided in Table IV is not intended to be limiting. Various modifications of the culture medium may be made by those skilled in the art, in view of practical and economic considerations, such as the scale of culture and local supply of media components.

The process is initiated by inoculating each 100 ml of medium with 1 ml of an inoculum of the selected yeast strain(s) at a cell density of $10^2$–$10^5$ cell/ml, preferably $3 \times 10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 1087–1097 MHz, preferably about at 1092, more preferably in the range of 1092.346 to 1092.428 MHz, and most preferably at 1092.387 MHz. The amplitude used can be in the range of 1000–2000 mV, preferably at about 1530 mV. After this first period of culture, the yeast cells are further incubated under substantially the same conditions for approximately another 24 hours, except that the amplitude is increased to a higher level in the range of 4000–5000 mV, preferably to about 4720 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stimng and/or bubbling.

At the end of the culturing process, the C-decomposing yeast cells may be recovered from the culture by various methods known in the art, and stored at a temperature below about 0–4° C. The C-decomposing yeast cells may also be dried and stored in powder form.

Any methods known in the art can be used to test the cultured yeast cells for their ability to decompose complex-carbon containing substances. In one embodiment, 1 ml of the prepared yeast culture is inoculated into 30 ml of a medium according to Table IV. The culture is incubated at a temperature in the range of 20–28° C. for 24–56 hours. The amount of simple carbohydrates in the culture can then be determined by any methods known in the art, including but not limited to chromatography and molecular fluorescence spectroscopy. Preferably, the amount of simple carbohydrates in the culture is increased by at least 10 mg for each gram of yeast dry weight. For example, after activation, the amount of simple carbohydrates in a culture of *Saccharomyces cerevisiae* Hansen AS2.406 can reach 27200 mg/g.

5.5. GROWTH FACTORS PRODUCING YEAST CELL COMPONENT

The growth factors producing (GP-producing) yeast of the present invention produces vitamins and other nutrients, such as but not limited to, vitamin B-1, riboflavin (vitamin B-2), vitamin B-12, niacin (B-3), pyridoxine (B-6), pantothenic acid (B-5), folic acid, biotin, para-aminobenzoic acid, choline, inositol, in such amounts that can support the growth of other yeast strains. Such growth factors are produced by yeast during the fermentation process.

In the present invention, the ability of yeast to overproduce growth factors is activated or enhanced, and the resulting GP-producing yeast cells can be used as a component of the biological fertilizer composition of the invention.

According to the present invention, yeast cells that are capable of GP-producing are prepared by culturing the cells in the presence of an electromagnetic field in an appropriate culture medium. The frequency of the electromagnetic field for activating or enhancing GP-production in yeasts can generally be found in the range of 1300 MHz–1500 MHz.

After the yeast cells have been cultured for a sufficient period of time, the cells can be tested for their ability to produce growth factors by methods well known in the art.

The method of the invention for making the GP-producing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches., can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.51% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $NH_4NO_3$, $K_2HPO_4$, $CaCO_3$, $MgSO_4$, NaCl, and $CaSO_4$.

TABLE V

Composition for a culture medium for GP-producing yeast

| Medium Composition | Quantity |
| --- | --- |
| Starch | 8.0 g; Powder of >120 mesh |
| NaCl | 0.3 g |
| $MgSO_4 \cdot 7H_2O$ | 0.2 g |
| $CaCO_3 \cdot 5H_2O$ | 0.5 g |
| $CaSO_4 \cdot 2H_2O$ | 0.2 g |
| $NH_4NO_3$ | 0.3 g |
| $K_2HPO_4$ | 0.8 g |
| Autoclaved water | 1000 ml |

It should be noted that the composition of the media provided in Table V is not intended to be limiting. Various modifications of the culture medium may be made by those skilled in the art, in view of practical and economic considerations, such as the scale of culture and local supply of media components.

The process is initiated by inoculating each 100 ml of medium with 1 ml of an inoculum of the selected yeast strain(s) at a cell density of $10^2$–$10^5$ cell/ml, preferably $3 \times 10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 1382–1392 MHz, preferably at about 1387 MHz, more preferably in the range of 1387.517 to 1387.595 MHz, and most preferably at 1387.556 MHz. The amplitude used can be in the range of 1000–200 mV, preferably at about 1620 mV. After this first period of culture, the yeast cells are further incubated under substantially the same conditions for approximately another 24 hours, except that the amplitude is increased to a higher level in the range of 4000–5000 mV, preferably to about 4830 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m³, preferably 0.4 mol/m³. The oxygen level can be controlled by any conventional means known to one skilled in the art, including but not limited to stirring and/or bubbling.

At the end of the culturing process, the GP-producing yeast cells may be recovered from the culture by various methods known in the art, and stored at a temperature below about 0–4° C. The GP-producing yeast cells may also be dried and stored in powder form.

Any methods known in the art can be used to test the cultured yeast cells for their ability to overproduce growth factors. In one embodiment, 1 ml of the prepared yeast culture is inoculated into 30 ml of a medium according to Table V. The culture is incubated at a temperature in the range of 20–28° C. for 32–48 hours. The amount of growth factors as represented by the total amount of vitamin B1, B2, B6, and B12 in the culture can then be determined by any methods known in the art, including but not limited to high performance liquid chromatography (HPLC). The amount of growth factors in the culture is increased by at least 10 mg for each gram of yeast dry weight. For example, after activation, the amount of vitamin B1, B2, B6, and B12 in a culture of *Saccharomyces cerevisiae* Hansen AS2.382 can reach an aggregate of 6120 mg/g.

5.6. ATP-PRODUCING YEAST CELL COMPONENT

The ATP-producing yeast of the present invention is capable of overproducing ATP in such amounts that can support the growth of other yeast strains in the biological fertilizer composition.

In the present invention, the ability of yeast to overproduce ATP is activated or enhanced, and the resulting ATP-producing yeast cells can be used as a component of the biological fertilizer composition of the invention.

According to the present invention, yeast cells that are capable of enhanced ATP-production are prepared by culturing the cells in the presence of an electric field in an appropriate culture medium. The frequency of the electromagnetic field for activating or enhancing ATP-production in yeasts can generally be found in the range of 1600 MHz–1800 MHz. After sufficient time is given for the cells to grow, the cells can be tested for their enhanced ability to produce ATP by methods well known in the art.

The method of the invention for making the ATP-producing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $CaCO_3$, $MgSO_4$, NaCl, and $CaSO_4$.

TABLE VI

Composition for a culture medium for ATP-producing yeast

| Medium Composition | Quantity |
| --- | --- |
| Starch | 10.0 g |
| NaCl | 0.2 g |
| $MgSO_4 \cdot 7H_2O$ | 0.2 g |
| $CaCO_3 \cdot 5H_2O$ | 0.8 g |
| $CaSO_4 \cdot 2H_2O$ | 0.2 g |
| $NH_4NO_3$ | 0.2 g |
| $K_2HPO_4$ | 0.5 g |
| Autoclaved water | 1000 ml |

It should be noted that the composition of the media provided in Table VI is not intended to be limiting. Various modifications of the culture medium may be made by those skilled in the art, in view of practical and economic considerations, such as the scale of culture and local supply of media components.

The process is initiated by inoculating each 100 ml of medium with 1 ml of an inoculum of the selected yeast strain(s) at a cell density of $10^2$–$10^5$ cell/ml, preferably $3 \times 10^2$–$10^4$ cell/ml. The process can be scaled up or down according to needs. The yeast culture is grown for about 12–24 hours, preferably for about 24 hours, in the presence of an electromagnetic field. The electromagnetic field, which can be applied by any means known in the art, has a frequency in the range of 1690–1700 MHz, preferably at about 1694 MHz, more preferably in the range of 1694.328 to 1694.402 MHz, and most preferably at 1694.365 MHz. The amplitude of the field is in the range of 1000–200 mV, preferably at about 1470 mV. After this first period of culture, the yeast cells are further incubated under substantially the same conditions for approximately another 24 hours, except that the amplitude is increased to a higher level in the range of 4000–5000 mV, preferably to about 4780 mV. An exemplary set-up of the culture process is depicted in FIG. 1. The process of the invention is carried out at temperatures ranging from about 25° to 30° C.; however, it is preferable to conduct the process at 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the ATP-producing yeast cells may be recovered from the culture by various methods known in the art, and stored at a temperature below about 0–4° C. The ATP-producing yeast cells may also be dried and stored in powder form.

Any methods known in the art can be used to test the cultured yeast cells for their ability to overproduce ATP. In one embodiment, 1 ml of the prepared yeast culture is inoculated into 30 ml of a medium according to Table VI. The culture is incubated at a temperature in the range of 20–28° C. for 36–56 hours. The amount of ATP in the culture can then be determined by any methods known in the art, including but not limited to HPLC. The amount of ATP produced is increased by at least about 10 mg for each gram of yeast dry weight. For example, after activation, the amount of ATP produced in a culture of *Saccharomyces cerevisiae* Hansen strain AS2.16 can reach about 3320 mg/g.

5.7. FORMATION OF SYMBIOSIS-LIKE RELATIONSHIPS

In another embodimemt of the present invention, yeast strains with the newly activated or enhanced ability to fix nitrogen, decompose phosphorus-containing minerals or compounds, decompose insoluble potassium-containing minerals or compounds, and decompose complex carbon materials as described in Sections 5.1–5.4 are combined and cultured so that they form a symbiosis-like relationship whereby they can grow together without substantially relying on outside supplies of biological available nitrogen, phosphorus, potassium, and carbon nutrients. The nutrients needed for growth are supplied by the respective nutrient-producing yeast strain within the fertilizer composition by converting biologically-unavailable nutrients from various sources into available nutrients. The activity of each of the yeast strains in producing the respective types of nutrient relates in part to the needs of other yeast cells as well as the plants. As a result, soluble, biologically-available nutrients will be converted when needed, thereby avoiding excess losses due to, for example, leaching.

The optional process which can be used to improve the performance of the biological fertilizer is described as follows. Four strains of yeasts prepared according to Sections 5.1–5.4 are mixed and cultured in the presence of an electromagnetic field in an appropriate liquid medium. The medium contains nitrogen, phosphorus, potassium, and carbon nutrients in biologically unavailable forms. As non-limiting examples, atmospheric nitrogen is used as the source of nitrogen nutrient, powder of phosphate rock is used as the source of phosphorus nutrient, powder of potassium mica is used as the source of potassium nutrient, and powdered cellulose is used as the source of complex carbon nutrient. Other forms of insoluble phosphorus- and potassium-containing substances and complex carbon compounds may also be used in place of or in combination with any of the above-identified minerals as sources of phosphorus, potassium, and carbon nutrients. Among the inorganic salts which can be incorporated in the culture media are the customary salts capable of yielding sodium, calcium, sulfate, carbonate, and like ions. Non-limiting examples of nutrient inorganic salts are $CaCO_3$, $MgSO_4$, NaCl, and $CaSO_4$.

TABLE VII

Composition for a culture medium for formation of symbiosis-like relation

| Medium Composition | Quantity |
| --- | --- |
| NaCl | 0.5 g |
| $MgSO_4 \cdot 7H_2O$ | 0.4 g |
| $CaCO_3 \cdot 5H_2O$ | 3.0 g |
| $CaSO_4 \cdot 2H_2O$ | 0.3 g |
| Yeast extract paste | 0.3 g |
| Potassium mica | 1.2 g; Powder of >200 mesh |
| Rock phosphate | 1.2 g; Powder of >200 mesh |
| Cellulose | 5.0 g; Powder of >200 mesh |
| Autoclaved water | 1000 ml |

It should be noted that the composition of the media provided in Table VII is not intended to be limiting. Various modifications of the culture medium may be made by those skilled in the art, in view of practical and economic considerations, such as the scale of culture and local supply of media components.

The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling. The process of the invention is carried out at temperatures ranging from about 25° to 30° C.; however, it is preferable to conduct the process at 28° C. The process is initiated in sterilized medium by inoculating typically about 20 ml of each inoculum of the four strains of yeast cells, each at a cell density of about $10^8$ cell/ml. The optional process can be scaled up or down according to needs.

The yeast culture is grown for 12–72 hours, preferably for about 48 hours, in the presence of four independent electromagnetic fields. The electromagnetic fields, which can be applied by a variety of means, each has the following respective frequencies: (1) in the range of 860 to 870 MHz, preferably at about 865 MHz, more preferably in the range of 865.522 to 865.622 MHz, and most preferably at 865.572 MHz, for nitrogen-fixing; (2) in the range of 360–370 MHz, preferably at about 366 MHz, more preferably in the range of 366.199 to 366.287 MHz, and most preferably at 366.243 MHz, for phosphorus-decomposing; (3) in the range of 250–260 MHz, preferably at about 255 MHz, more preferably in the range of 255.388 to 255.462 MHz, and most preferably at 255.425 MHz, for potassium-decomposing; and (4) in the range of 1087–1097 MHz, preferably about at 1092, more preferably in the range of 1092.346 to 1092.428 MHz, and most preferably at 1092.387 MHz, for complex carbon-decomposing. The amplitude of each electromagnetic field is repeatedly cycled between 0–300 mV, preferably between 20–1800 mV, in steps of 1 mV at a rate of 18–23 minutes per complete cycle. An exemplary set-up of the culture process is depicted in FIG. 2.

5.8. SOIL ADAPTATION

The yeast strains of the invention must also be able to grow and perform their respective functions in various types of soils. The ability of the yeast strains to survive and grow can be enhanced by adapting the yeast strains of the invention to a particular soil condition.

In another embodiment of the invention, yeast cells prepared according to any one of Sections 5.1–5.6 can be cultured separately or in a mixture in a solid or semi-solid medium containing soil from one or more soil sources. This optional process which can be used to improve the performance of the biological fertilizer is described by way of an example as follows.

A suspension containing 10 ml of yeasts at a density of $10^6$ cell/ml is mixed with a 1000 cm$^3$ of the soil medium. The process can be scaled up or down according to needs. The mixture of yeast and soil is cultured for about 48–96 hours, preferably for about 48 hours, in the presence of an electromagnetic field. The electromagnetic field, which can be applied by a variety of means, has a frequency that, depending on the strain of yeast, corresponds to one of the frequencies described in Sections 5.1–5.6. A field amplitude in the range of 100–3000 mV, preferably 2100 mV, can be used. The culture is incubated at temperatures that cycle between about 3° C. to about 48° C. For example, in a typical cycle, the temperature of the culture may start at 35–48° C. and be kept at this temperature for about 1–2 hours, then adjusted up to 42–45° C. and kept at this temperature for 1–2 hours, then adjusted to 26–30° C. and kept at this temperature for about 2–4 hours, and then brought down to 5 –10° C. and kept at this temperature for about 1–2 hours, and then the temperature may be raised again to 35–45° C. for another cycle. The cycles are repeated until the process is completed. After the last temperature cycle is completed, the temperature of the culture is lowered to 3–4° C. and kept at this temperature for about 5–6 hours. After adaptation, the yeast cells may be isolated and recovered from the medium by conventional methods, such as filtration. The adapted yeast cells can be stored under 4° C. An exemplary set-up of the culture process is depicted in FIG. 3.

5.9. SEPARATION OR ENRICHMENT OF YEAST CELLS

Yeast cells that have been adapted to form a symbiosis-like relationship according to Section 5.7. can be separated or enriched in such a way that each strain of yeast cells keep their acquired or enhanced functions. Separation of yeast cells is carried out according to methods described in U.S. Pat. No. 5,578,486 and Chinese patent publication CN I 11031 7A which are incorporated herein by reference in its entirety. The frequency used for activating the yeast cells may be used during the separation process. The separated yeast cells can then be dried, and stored.

5.10. MANUFACTURE OF THE BIOLOGICAL FERTILIZERS

In addition to yeast cell components, various organic and inorganic raw materials can also be included in the biological fertilizer compositions of the invention, The preparation of such materials as well as the steps involved in the manufacture of the biological fertilizer are described herein.

5.10.1. Preparation of the Organic and Inorganic Substrate Components

A wide range of organic and inorganic materials can be used in the biological fertilizer compositions of the present invention. Organic materials, such as but not limited to coal-mine waste and weathered coal, or any materials that contain more than 20% of organic substances, can be used as sources of carbon to support the growth of plants and yeasts. Combinations and mixtures of such organic materials can also be used. Organic compounds present in such materials are decomposed by the yeast capable of breaking complex or high molecular weight carbon-chain molecules into simple carbon compounds so that they can be used by plants and other yeast cells in the fertilizer.

Inorganic materials, such as but not limited to phosphate rock and potassium mica, are included as sources of phosphorus and potassium respectively. Other phosphorous- or potassium-containing materials and minerals can also be used. These inorganic compounds are decomposed by K-decomposing and P-decomposing yeast cells into biologically available potassium and biologically available phosphorus that can be used by the growing plants as well as the yeast cells in the fertilizer. Any organic or inorganic material may be used alone or in combination or in substitution with any other materials in the present invention. Alternatively, one or more organic or inorganic ingredients may be omitted, or substituted by another if it is deemed desirable by the particular application. For example, potassium mica can be omitted if the soil contains sufficient potassium minerals.

The organic and inorganic materials used in the invention should not contain amounts of toxic substances or microorganisms that can inhibit the growth of the yeast cells or plants.

The organic and inorganic components in the present invention are ground into suitable forms and sizes before incorporated into the fertilizer. Typically, the organic or inorganic material is conveyed into a crusher where it is broken up into pieces of ≦5 cm in diameter. Any conventional crusher or equivalent machines can be used for this purpose. The pieces are then transferred to a grinder by any conveying means and ground to a powder of ≧150 mesh. Any grinder that allows fine grinding can be used for this purpose. The powder is then conveyed to an appropriate storage tank for storage until use with other components of the fertilizer. A schematic illustration of the grinding process is shown in FIGS. 4 and 5.

5.10.2. Fermentation Process Using Growth Factor-Producing Yeast

In the present invention, the preparation of GP-producing yeast is carried out in a fermentation process using as seed the activated yeast strain as described in Section 5.5. A schematic of the fermentation process is illustrated in FIG. 6.

The fermentation medium is prepared according to a ratio of 2.5 liters of water per kilogram of starch. Clean water, preferably water free of any microorganisms, is used to prepare the fermentation medium. The fermentation is carried out at a temperature between 20–30° C., preferably between 25–28° C., in a clean environment and in a space where there are no strong sources of electromagnetic fields, such as power lines and power generators. Any equipments that contact the fermentation broth, including reactors, pipelines, and stirrers, must be throughly cleaned before each use. The fermentation process normally lasts about 60–72 hours, depending on the fermentation temperature. At least 90% of the fermentation substrate is fermented. Fermentation is preferably conducted under semi-aerobic conditions or conditions in which the oxygen level is about 20–60% of the maximal soluble oxygen concentration. The oxygen level can be controlled by any conventional means known to one skilled in the art, including but not limited to stirring and/or bubbling. After fermentation, the cell counts should reach about $2\times10^{10}$ cells/ml. The fermentation broth is kept at a temperature in the range of 15–28° C. and must be used within 24 hours. Alternatively, the GP-producing yeasts can be drained, dried and stored in powder form.

5.10.3. Fermentation Process Using ATP-Producing Yeast

In the present invention, the preparation of ATP-producing yeast is carried out by a fermentation process using as seed the adapted yeast strain as described in Section 5.6. A schematic of the fermentation process is illustrated in FIG. 6.

The fermentation medium is prepared according to a ratio of 2.5 liters of water per kilogram of starch. Clean water, preferably water free of any microorganisms, most preferably autoclaved water, is used to prepare the fermentation media. The fermentation is carried out at a temperature between 20–30° C., preferably between 25–28° C., in a clean environment and in a space where there are no strong sources of electromagnetic fields, such as power lines and power generators. Any equipments that contact the fermentation broth, including reactors, pipelines, and stirrers, must be throughly cleaned before each use. The fermentation process normally lasts about 60–72 hours, depending on the fermentation temperature. At least 90% of the fermentation substrate is fermented. Fermentation is preferably conducted under semi-aerobic conditions or conditions in which the oxygen level is about 20–60% of the maximal soluble oxygen concentration. The oxygen level can be controlled by any conventional means known to one skilled in the art, including but not limited to stirring and/or bubbling. After fermentation, the cell counts should reach about $2\times10^{10}$ cells/ml. The fermentation broth is kept at a temperature in the range of 15–28° C. and must be used within 24 hours. Alternatively, the ATP-producing yeasts can be drained, dried and stored in powder form.

5.10.4. Preparation of Mixture of Raw Materials

Organic and inorganic raw materials are mixed in exemplary proportions as shown in Table VIII. Appropriate amount of organic and inorganic materials prepared according to Section 5.10.1 and starch are conveyed to a mixer. Any conventional mixer, such as but not limited a rotary drum mixer, can be used. The mixing tank is rotated constantly so that powders of inorganic material, organic material, and starch are mixed evenly. The mixture is then conveyed to a storage tank. The procedure for mixing organic and inorganic substrate material is illustrated in FIG. 7.

TABLE VIII

Ratio of raw materials

| Material | Percentage | Requirement |
|---|---|---|
| Powder of organic materials | 60–71% | ≧150 mesh, water content ≦5% |
| Powder of inorganic materials | 15–20% | ≧150 mesh, water content ≦3% |
| Starch | 10–15% | regular starch powder, water content ≦8% |

5.10.5. Preparation of Yeast Mixture

A yeast mixture is prepared in the exemplary proportions as shown in Table IX. Appropriate amounts of the six yeast strains in dried powder form prepared according to Section 5.1–5.6 are conveyed to a mixing tank. The yeasts are allowed to mix for about 10–20 minutes. The mixture is then transferred to a storage tank. Any equipments used for mixing yeasts, including the mixing tank and the storage tank, must be throughly cleaned, preferably sterilized, before each use. The yeast mixture is stored at a temperature below 20° C. and must be used within 24 hours. The procedure for mixing yeasts is illustrated in FIG. 8. Alternatively, the mixture of six yeasts can be dried and stored in powder form.

TABLE IX

Ratio of microorganisms

| Yeast | Quantity | Percentage (dry weight) | Note |
|---|---|---|---|
| Nitrogen-fixing yeast | 1.0–2.0 kg | 0.1–0.2% | Dry yeast powder |
| Phosphorus-decomposing yeast | 1.0–2.0 kg | 0.1–0.2% | Dry yeast powder |
| Potassium-decomposing yeast | 1.0–2.0 kg | 0.1–0.2% | Dry yeast powder |
| Carbon-decomposing yeast | 1.0–2.0 kg | 0.1–0.2% | Dry yeast powder |
| Growth factor producing yeast | 25 L | 1% | Yeast fermentation broth |
| ATP-producing yeast | 75 L | 3% | Yeast fermentation broth |

5.10.6. Manufacture of Biological Fertilizer

The biological fertilizer of the present invention is produced by mixing the yeast mixture of Section 5.10.5 and the mixture of the organic and inorganic materials of Section 5.10.1 at a ratio according to Table X. For example, the yeasts and the organic and inorganic materials are conveyed to a granulizer to form granules. The granules of the fertilizer are then dried in a two-stage drying process. During the first drying stage, the fertilizer is dried in a first dryer at a temperature not exceeding 65° C. for a period of time not exceeding 10 minutes so that yeast cells quickly become dormant. The fertilizer is then send to a second dryer and dried at a temperature not exceeding 70° C. for a period of time not exceeding 30 minutes to further remove water. After the two stages, the water content should be lower than 5%. It is preferred that the temperatures and drying times be adhered to in both drying stages so that yeast cells do not lose their vitality and functions. The fertilizer is then cooled to room temperature. The fertilizer may also be screened in a separator so that fertilizer granules of a preferred size are selected. Any separator, such as but not limited to a turbo separator with adjustable speed and screen sizes, can be used. The fertilizer of the selected size is then sent to a bulk bag filler for packing.

The production process is illustrated in FIGS. 9–11. FIG. 9 is a schematic illustration of the procedure for producing the fertilizer from its components. FIG. 10 is a schematic illustration of the drying process. FIG. 11 is a schematic illustration of the cooling and packing process.

TABLE X

Composition of the biological fertilizer (for one metric ton of fertilizer)

| | Quantity | Percentage (dry weight) | Note |
|---|---|---|---|
| Mixture of raw materials | 952–956 kg | 95.2–95.4% | Dry weight |
| Mixture of yeasts | 100 L | 4.4–4.8% | Dry weight |

6. EXAMPLE

The following example demonstrates the manufacture of a biological fertilizer composition of the present invention. This example is a preferred embodiment of the present invention.

*Saccharomyces cerevisiae* Hansen strains having accession numbers AS2.501, AS2.535, AS2.441, AS2.406, AS2.382, and AS2.16, each of which is deposited in China General Microbiological Culture Collection Center (CGMCC), China Committee for Culture Collection of Microorganisms, were used to prepare the yeast cell components of the biological fertilizer. Yeast strain AS2.501 was cultured according to the method described in Section 5.1 for nitrogen-fixation. Yeast strain AS2.535 was cultured according to the method described in Section 5.2 for P-decomposition. Yeast strain AS2.441 was cultured according to the method described in Section 5.3 for K-decomposition. Yeast strain AS2.406 was cultured according to the method described in Section 5.4 for C-decomposition. Yeast strain AS2.382 was cultured according to the method described in Section 5.5 for growth factor-production. Yeast strain AS2.16 was cultured according to the method described in Section 5.6 for ATP-production.

Coal mine waste and phosphate rock were used as organic and inorganic materials respectively. The coal mine waste used in the example contained at least 30% of organic substances. The phosphate rock used in the example contained at least 25% of $P_2O_5$. Coal mine waste and phosphate rock were prepared according to Sections 5.10.1.

The production of growth factor-producing yeast was carried out in a fermentation process using as seed the activated yeast strain AS2.382 as described in Section 5.5. A schematic of the fermentation process is illustrated in FIG. 6. The fermentation medium was prepared according to a ratio of 2.5 liters of clean water per kilogram of starch. The fermentation medium was inoculated according to a ratio of 10 ml of seed solution per liter of medium. The fermentation was carried out at a temperature of 28±1° C. and an oxygen concentration of 0.4 mol/m$^3$ in a clean environment where there were no sources of electromagnetic fields for about 48 hours. After fermentation, the cell counts reached about 2×10$^{10}$ cells/ml.

The production of ATP-producing yeast was carried out in a fermentation process using as seed the activated yeast strain AS2.16 as described in Section 5.6. A schematic of the fermentation process is illustrated in FIG. 6. The fermentation medium was prepared according to a ratio of 2.5 liters of clean water per kilogram of starch. The fermentation medium was inoculated according to a ratio of 10 ml of seed solution per liter of medium. The fermentation was carried out at a temperature of 28±1° C. and an oxygen concentration of 0.4 mol/m$^3$ in a clean environment where there were no sources of electromagnetic fields for about 56 hours. After fermentation, the cell counts reached about 2×10$^{10}$ cells/ml.

The mixture of raw materials was prepared according to Table XI and the procedure in Section 5.10.4.

TABLE XI

Ratio of raw materials

| Material | Percentage | Requirement |
|---|---|---|
| Powder of coal mine waste | 65% | ≧150 mesh, water content ≦5% |
| Powder of phosphate rock | 20% | ≧150 mesh, water content ≦3% |
| Starch | 15% | regular starch powder, water content ≦8% |

The yeast mixture was prepared according to Table XII and the procedure described in Section 5.10.5.

TABLE XII

Ratio of yeasts (for 1 metric ton of fertilizer)

| Yeast | Quantity | Percentage (dry weight) | Note |
|---|---|---|---|
| Nitrogen-fixing yeast AS2.502 | 2.0 kg | 0.2% | Dry yeast powder |
| Phosphorus-decomposing yeast AS2.535 | 2.0 kg | 0.2% | Dry yeast powder |
| Potassium-decomposing yeast AS2.441 | 2.0 kg | 0.2% | Dry yeast powder |
| Carbon-decomposing yeast AS2.406 | 2.0 kg | 0.2% | Dry yeast powder |
| Growth factor producing yeast AS2.382 | 25 L | 1% | Yeast fermentation broth |
| ATP producing yeast AS2.16 | 75 L | 3% | Yeast fermentation broth |

The biological fertilizer was produced by mixing the yeast mixture, the organic and inorganic materials at a ratio according to Table XIII. The mixed yeasts and organic and inorganic materials were conveyed to a granulizer to form granules. The granules of the fertilizer were then dried in a two stage drying process. During the first drying stage, the fertilizer was dried in a first dryer at a temperature not exceeding 60±2° C. for a period of 5 minutes so that yeast cells quickly became dormant. The fertilizer was then sent to a second dryer and dried at a temperature not exceeding 65±2° C. for a period of 8 minutes to further remove water. The fertilizer was then cool to room temperature. The fertilizer was then sent to a bulk bag filler for packing.

TABLE XIII

Fertilizer composition (for 1 metric ton of fertilizer)

|  | Quantity | Percentage (dry weight) | Note |
|---|---|---|---|
| Raw material mixture | 952 kg | 95.2% | Dry weight |
| Yeast mixture | 100 L | 4.8% | Dry weight |

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A biological fertilizer composition comprising at least one of the following yeast cell components:
   (a) a first yeast cell component comprising a first plurality of yeast cells characterized by an enhanced ability to fix nitrogen as a result of having been cultured in a first electromagnetic field having a frequency in the range of 860 to 870 MHz and an amplitude in the range of 1000 to 5000 mV, as compared to yeast cells not having been so cultured;
   (b) a second yeast cell component comprising a second plurality of yeast cells characterized by an enhanced ability to decompose phosphorous compounds as a result of having been cultured in a second electromagnetic field having a frequency in the range of 360 to 370 MHz and an amplitude in the range of 1000 to 5000 mV, as compared to yeast cells not having been so cultured; or
   (c) a third yeast cell component comprising a third plurality of yeast cells characterized by an enhanced ability to decompose potasssium compounds as a result of having been cultured in a third electromagnetic field having a frequency in the range of 250 to 260 MHz and an amplitude in the range of 1000 to 5000 mV, as compared to yeast cells not having been so cultured.

2. The biological composition of claim 1 further comprising:
   (d) a fourth yeast cell component comprising a fourth plurality of yeast cells characterized by an enhanced ability to convert complex carbon molecules to simple carbohydrates as a result of having been cultured in a fourth electromagnetic field having a frequency in the range of 1087 to 1097 MHz and an amplitude in the range of 1000 to 5000 mV, as compared to yeast cells not having been so cultured;
   (e) a fifth yeast cell component comprising a fifth plurality of yeast cells characterized by an ability to overproduce growth factors as a result of having been cultured in a fifth electromagnetic field having a frequency in the range of 1382 to 1392 MHz and an amplitude in the range of 1000 to 5000 mV, as compared to yeast cells not having been so cultured; and
   (f) a sixth yeast cell component comprising a sixth plurality of yeast cells characterized by an ability to overproduce adenosine triphosphate as a result of having been cultured in a sixth electromagnetic field having a frequency in the range of 1690 to 1700 MHz and an amplitude in the range of 1000 to 5000 mV, as compared to yeast cells not having been so cultured.

3. The biological fertilizer composition of claim 2 further comprising an organic substrate component, an inorganic substrate component, or both organic and inorganic substrate components.

4. The biological fertilizer composition of claim 2 wherein each yeast cell component separately comprises yeast cells that belongs to a genus selected from the group consisting of Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis; Geotrichum, Hansenula, Kloeckera, Lipomyces, Pichia, Rhodosporidium, and Rhodotorula.

5. The biological fertilizer composition of claim 2 wherein each yeast cell component comprises cells of a species of yeast selected from the group consisting of *Saccharomyces cerevisiae, Saccharomyces chevalieri, Saccharomyces delbrueckii, Saccharomyces exiguus, Saccharomyces fermentati, Saccharomyces logos, Saccharomyces mellis, Saccharomyces microellipsoides, Saccharomyces oviformis, Saccharomyces rosei, Saccharomyces rouxii, Saccharomyces sake, Saccharomyces uvarum Beijer, Saccharomyces willianus*, Saccharomyces sp., *Saccharomyces ludwigii, Saccharomyces sinenses, Saccharomyces bailii, Saccharomyces carlsbergensis, Schizosaccharomyces octosporus, Schizosaccharomyces pombe, Sporobolomyces roseus, Sporobolomyces salmonicolor, Torulopsis candida, Torulopsis famta, Torulopsis globosa, Torulopsis inconspicua, Trichosporon behrendoo, Trichosporon capitatum, Trichosporon cutaneum, Wickerhamia fluoresens, Ashbya gossypii, Blastomyces dermatitidis, Candida albicans, Candida arborea, Candida guillermondii, Candida Krusei, Candida lambica, Candida lipolytica, Candida parakrusei, Candida parapsilosis, Candida parapsilosis, Candida pseudotropicalis, Candida pulcherrima, Candida robusta, Candida rugousa, Candida utilis, Citeromyces matritensis, Crebrothecium ashbyii, Cryptococcus laurentii, Cryptococcus neoformans, Debaryomyces hansenii, Debaryomyces kloeckeri, Endomycopsis fibuligera, Eremothecium ashbyii, Geotrichum candidum, Geotrichum ludwigii, Geotrichum robustum, Geotrichum suaveolens, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia farinosa, Pichia membranaefaciens, Rhodosporidium toruloides, Rhodotorula aurantiaca, Rhodotorula glutinis, Rhodotorula minuta, Rhodotorula rubar*, and *Rhodotorula sinesis*.

6. The biological fertilizer composition of claim 2 wherein each yeast cell component comprises cells of *Saccharomyces cerevisiae*.

7. The biological fertilizer composition of claim 2 wherein the yeast cells of each yeast cell component are separately cells of the yeast *Saccharomyces cerevisiae* Hansen deposited at China General Microbiological Culture Collection Center having an accession number selected from the group consisting of AS2.501, AS2.535, AS2.441, AS2.406, AS2.382, and AS2.16.

8. The biological fertilizer composition of claim 4 which comprises yeast cell components (a), (b), and (c) of claim 1.

9. The biological fertilizer composition of claim 8 further comprising an organic substrate component, an inorganic substrate component, or both an organic and an inorganic substrate component.

10. The biological fertilizer composition of claim 9 which comprises about 0.1 to 0.2% by weight of yeast cell component (a), about 0.1 to 0.2% by weight of yeast cell component (b), about 0.1 to 0.2% by weight of yeast cell component (c), about 0.1 to 0.2% by weight of yeast cell component (d), about 1% by weight of yeast cell component (e), about 3% by weight of yeast cell component (f); about 65% by weight of organic substrate component; about 19% by weight of inorganic substrate component; and about 14% by weight of starch.

11. A composition comprising a plurality of yeast cells characterized by an enhanced ability of the yeast cells to fix nitrogen as a result of having been cultured in the presence of an electromagnetic field having a frequency in the range of 850 to 860 MHz and an amplitude in the range of 1000 to 5000 mV, as compared to yeast cells not having been so cultured.

12. A composition comprising a plurality of yeast cells characterized by an enhanced ability of the yeast cells to decompose phosphorus compounds as a result of having been cultured in the presence of an electromagnetic field having a frequency in the range of 360 to 370 MHz and an amplitude in the range of 1000 to 5000 mV, as compared to yeast cells not having been so cultured.

13. A composition comprising a plurality of yeast cells characterized by an enhanced ability of the yeast cells to decompose potassium compounds as a result of having been cultured in the presence of an electromagnetic field having a frequency in the range of 250 to 260 MHz and an amplitude in the range of 1000 to 5000 mV, as compared to yeast cells not having been so cultured.

14. A composition comprising a plurality of yeast cells characterized by an enhanced ability of the yeast cells to convert complex carbon molecules to simple carbohydrates as a result of having been cultured in the presence of an electromagnetic field having a frequency in the range of 1087 to 1097 MHz and an amplitude in the range of 1000 to 5000 mV, as compared to yeast cells not having been so cultured.

15. A composition comprising a plurality of yeast cells characterized by an enhanced ability of the yeast cells to overproduce growth factors as a result of having been cultured in the range of 1382 to 1392 MHz and an amplitude in the range of 1000 to 200 mV, as compared to yeast cells not having been so cultured.

16. A composition comprising a plurality of yeast cells characterized by an enhanced ability of the yeast cells to overproduce adenosine triphosphate as a result of having been cultured in the presence of an electromagnetic field having a frequency in the range of 1690 to 1700 MHz and an amplitude in the range of 1000 to 5000 mV, as compared to yeast cells not having been so cultured.

17. The composition of claim 11, 12, 13, 14, 15, or 16 wherein the yeast ells are cells of *Saccharomyces cerevisiae*.

18. A biological fertilizer composition comprising
  (i) at least one of the following yeast cell components:
    (a) a first yeast cell component comprising a first plurality of yeast cells characterized by an enhanced ability of the yeast cells to fix nitrogen as a result of having been cultured in a first electromagnetic field having a frequency of about 865.522 MHz and an amplitude of about 1250 mV for a period of 24 hours and a second electromagnetic field having a frequency of about 865.522 MHz and an amplitude of about 4656 mV for a period of 24 hours, as compared to yeast cells not having been so cultured;
    (b) a second yeast cell component comprising a second plurality of yeast cells characterized by an enhanced ability of the yeast cells to decompose phosphorus compounds as a result of having been cultured in a first electromagnetic field having a frequency of about 366.243 MHz and an amplitude of about 1230 mV for a period of 24 hours and a second electromagnetic field having a frequency of about 366.243 MHz and an amplitude of about 4570 mV for a period of 24 hours, as compared to yeast cells not having been so cultured; or
    (c) a third yeast cell component comprising a third plurality of yeast cells characterized by an enhanced ability of the yeast cells to decompose potassium compounds as a result of having been cultured in a first electromagnetic field having a frequency of about 255.425 MHz and an amplitude of about 1340 mV for a period of 24 hours and a second electromagnetic field having a frequency of about 255.425 MHz and an amplitude of about 4850 mV for a period of 24 hours, as compared to yeast cells not having been so cultured;
  (ii) a fourth yeast cell component comprising a fourth plurality of yeast cells characterized by an enhanced ability of the yeast cells to convert complex carbon molecules to simple carbohydrates as a result of having been cultured in a first electromagnetic field having a frequency of about 1092.387 MHz and an amplitude of about 1530 mV for a period of 24 hours and a second electromagnetic field having a frequency of about 1092.387 MHz and an amplitude of about 4720 mV for a period of 24 hours, as compared to yeast cells not having been so cultured;
  (iii) a fifth yeast cell component comprising a fifth plurality of yeast cells characterized by an enhanced ability of the yeast cells to overproduce growth factors as a result of having been cultured in a first electromagnetic field having a frequency of about 1387.556 MHz and an amplitude of about 1620 mV for a period of 24 hours and a second electromagnetic field having a frequency of about 1387.556 MHz and an amplitude of about 4830 mV for a period of 24 hours, as compared to yeast cells not having been so cultured; and
  (iv) a sixth yeast cell component comprising a sixth plurality of yeast cells characterized by an enhanced ability of the yeast cells to overproduce adenosine triphosphate as a result of having been cultured in a first electromagnetic field having a frequency of about 1694.365 MHz and an amplitude of about 1470 mV for a period of 24 hours and a second electromagnetic field having a frequency of about 1694.365 MHz and an amplitude of about 4780 mV for a period of 24 hours, as compared to yeast cells not having been so cultured;
wherein said yeast cell components comprise cells of *Saccharomyces cerevisiae*.

19. The biological fertilizer composition of claim 18 wherein the first yeast cell component comprises cells of the yeast strain *Saccharomyces cerevisiae* Hansen AS2.501, the second yeast cell component comprises cells of the yeast strain *Saccharomyces cerevisiae* Hansen AS2.535, the third yeast cell component comprises cells of the yeast strain *Saccharomyces cerevisiae Hansen* AS2.441, the fourth yeast cell component comprises cells of the yeast strain *Saccharomyces cerevisiae* Hansen AS2.406, the fifth yeast cell component comprises cells of the yeast strain *Saccharomyces cerevisiae* Hansen AS2.382, and the sixth yeast cell component comprises cells of the yeast strain *Saccharomyces cerevisiae* Hansen AS2.16.

20. The biological fertilizer composition of claim 18, wherein the pluralities of yeast cells are dried.

* * * * *

UNITED STATES PATENT AND TRADEMARK OFFICE
CERTIFICATE OF CORRECTION

PATENT NO. : 6,416,982 B1
DATED : July 9, 2002
INVENTOR(S) : Lingyu Zhang

It is certified that error appears in the above-identified patent and that said Letters Patent is hereby corrected as shown below:

<u>Column 5,</u>
Line 54, "camalitite" should be -- carnalitite --.

<u>Column 7,</u>
Line 29, "AS2.2 85" should be -- AS2.285 --.
Line 30, "*delhrueckii*" should be -- *delbrueckii* --.
Line 42, "*Saccharomyees*" should be -- *Saccharomyces* --.

<u>Column 9,</u>
Line 44, "V. 20110-2209" should be -- VA 20110-2209 --.

<u>Column 14,</u>
Line 61, "1000 to 200 mV" should be -- 1000 to 2000 mV --.

<u>Column 15,</u>
Line 31, "cornpound-decomposing" should be -- compound-decomposing --.

<u>Column 17,</u>
Line 6, "*Saccharomyees*" should be -- *Saccharomyces* --.
Line 8, "CARBON-DECONPOSING" should be -- CARBON-DECOMPOSING --.

<u>Column 19,</u>
Line 54, "1000 to 200 mV" should be -- 1000 to 2000 mV --.

<u>Column 21,</u>
Line 31, "1000 to 200 mV" should be -- 1000 to 2000 mV --.

UNITED STATES PATENT AND TRADEMARK OFFICE
CERTIFICATE OF CORRECTION

PATENT NO.   : 6,416,982 B1
DATED        : July 9, 2002
INVENTOR(S)  : Lingyu Zhang It is certified that error appears in the above-identified patent and that said Letters Patent is hereby corrected as shown below:

<u>Column 23,</u>
Line 23, "0-300 mV" should be -- 0-3000 mV --.

<u>Column 24,</u>
Lines 8-9, "CN I 11031 7A" should be -- CN 1110317A --.

Signed and Sealed this

Twenty-fourth Day of February, 2004

JON W. DUDAS
*Acting Director of the United States Patent and Trademark Office*